(12) United States Patent
Dreier et al.

(10) Patent No.: US 8,231,691 B2
(45) Date of Patent: Jul. 31, 2012

(54) AZO DYES

(75) Inventors: Romeo Dreier, Fehren (CH); Alfons Arquint, Basel (CH); Urs Lauk, Magstatt-le-Haut (FR); Patric Nowack, Steinen (DE)

(73) Assignee: Huntsman International LLC, The Woodlands, TX (US)

( * ) Notice: Subject to any disclaimer, the term of this patent is extended or adjusted under 35 U.S.C. 154(b) by 0 days.

(21) Appl. No.: 12/669,887

(22) PCT Filed: Jul. 8, 2008

(86) PCT No.: PCT/EP2008/058828
§ 371 (c)(1),
(2), (4) Date: Jan. 20, 2010

(87) PCT Pub. No.: WO2009/013122
PCT Pub. Date: Jan. 29, 2009

(65) Prior Publication Data
US 2010/0196676 A1   Aug. 5, 2010

(30) Foreign Application Priority Data

Jul. 20, 2007 (EP) .................................. 07112861

(51) Int. Cl.
*C09B 29/40* (2006.01)
(52) U.S. Cl. .............. 8/690; 8/639; 8/662; 8/666; 8/920
(58) Field of Classification Search .............. 8/662, 666, 8/690, 920, 639
See application file for complete search history.

(56) References Cited

U.S. PATENT DOCUMENTS

| 3,148,178 | A | * | 9/1964 | Wallace et al. | ................ 534/804 |
| 3,491,062 | A | | 1/1970 | Weaver et al. | |
| 3,491,082 | A | * | 1/1970 | Weaver et al. | ................ 534/777 |
| 4,650,861 | A | * | 3/1987 | Weaver et al. | ................ 534/777 |

FOREIGN PATENT DOCUMENTS

| DE | 2640764 | 3/1978 |
| GB | 1288397 | 9/1972 |

\* cited by examiner

*Primary Examiner* — Lorna M Douyon
*Assistant Examiner* — Amina Khan

(57) ABSTRACT

The present invention relates to disperse azo dyes based on a phthalimido-substituted aniline coupling component and an aromatic-carbocyclic or an aromatic-heterocyclic diazo component, to a process for the preparation of such dyes and to their use in the dyeing or printing of semi-synthetic and, especially, synthetic hydrophobic fiber materials, more especially textile materials.

15 Claims, No Drawings

AZO DYES

FIELD OF THE INVENTION

The present invention relates to disperse dyes having a phthalimido-substituted aniline coupling component, to a process for the preparation of such dyes and to their use in the dyeing or printing of semi-synthetic and, especially, synthetic hydrophobic fibre materials, more especially textile materials.

BACKGROUND OF THE INVENTION

Disperse azo dyes having an N-alkyl-phthalimide diazo component and an aniline coupling component have been known for a long time and are used in the dyeing of hydrophobic fibre materials. It has been found, however, that the dyeings or prints obtained using the dyes known at present do not in all cases meet current requirements, especially with regard to their fastness properties in respect of light, washing and perspiration. Particularly in the field of blue dyes there is a need for new dyes that give dyeings in brilliant shades having good fastness properties in respect of light, washing and perspiration.

It has now been found, surprisingly, that the dyes according to the invention meet the criteria mentioned above to a great extent.

SUMMARY OF THE INVENTION

The present invention accordingly relates to disperse dyes that yield dyeings having very good fastness to light, to washing and to perspiration and, in addition, exhibit good build-up both in the exhaust and thermosol processes and in textile printing. The dyes are also suitable for discharge printing.

DETAILED DESCRIPTION OF THE INVENTION

The dyes according to the invention correspond to formula

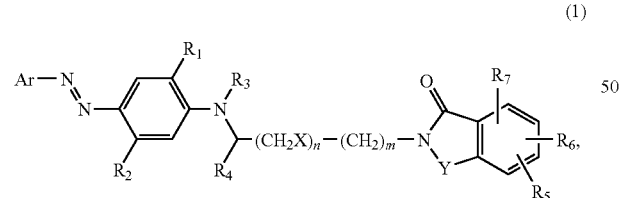

(1)

wherein Ar is a radical of formula (1a)-(1l)

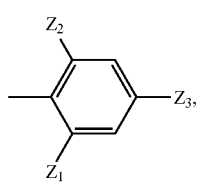

(1a)

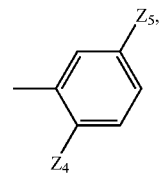

(1b)

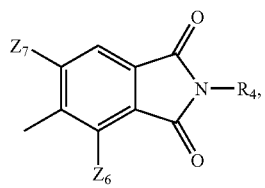

(1c)

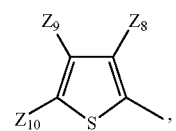

(1d)

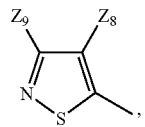

(1e)

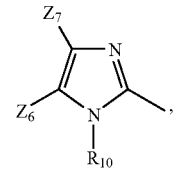

(1f)

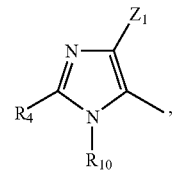

(1g)

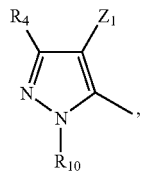

(1h)

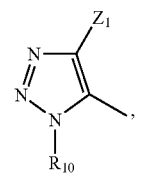

(1i)

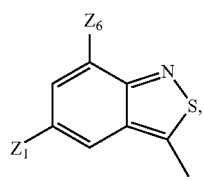

(1j)

-continued (1k)

(1l)

wherein
R$_1$ is hydrogen, C$_1$-C$_{12}$alkyl, C$_1$-C$_{12}$alkoxy or halogen,
R$_2$ is hydrogen, C$_1$-C$_{12}$alkyl, halogen or —NHCOR$_8$, wherein R$_8$ is C$_1$-C$_{12}$alkyl unsubstituted or substituted by one or more C$_1$-C$_{12}$alkoxy groups, hydroxyl groups, amino groups or halogen atoms; C$_5$-C$_{30}$aryl unsubstituted or substituted by one or more C$_1$-C$_{12}$alkyl groups, C$_1$-C$_{12}$alkoxy groups, hydroxyl groups, amino groups or halogen atoms; or C$_5$-C$_{30}$heteroaryl unsubstituted or substituted by one or more C$_1$-C$_{12}$alkyl groups, C$_1$-C$_{12}$alkoxy groups, hydroxyl groups, amino groups or halogen atoms,
R$_3$ is C$_1$-C$_{12}$alkyl unsubstituted or substituted by one or more C$_1$-C$_{12}$alkoxy groups, hydroxyl groups, amino groups, —COOR$_8$ groups, —OCOR$_8$ groups, wherein R$_8$ is as defined above, or halogen atoms; C$_2$-C$_{12}$alkenyl unsubstituted or substituted by one or more C$_1$-C$_{12}$alkoxy groups, hydroxyl groups, amino groups or halogen atoms; or C$_6$-C$_{36}$aralkyl unsubstituted or substituted by one or more C$_1$-C$_{12}$alkoxy groups, hydroxyl groups, amino groups or halogen atoms,
R$_4$ is hydrogen or C$_1$-C$_{12}$alkyl,
X is oxygen or sulfur,
n is 0 or 1,
m is a number from 1 to 5,
R$_2$ not being hydrogen or methyl when n=0 and m=1,
Y is —CO— or —SO$_2$—,
R$_5$, R$_6$ and R$_7$ are each independently of the others hydrogen, C$_1$-C$_{12}$alkyl, C$_1$-C$_{12}$alkoxy, halogen, —CN, —NO$_2$, —CF$_3$, —COOR$_9$ or —CONHR$_9$, wherein R$_9$ is C$_1$-C$_{12}$alkyl, C$_5$-C$_{30}$aryl or C$_5$-C$_{30}$heteroaryl,
R$_{10}$ is hydrogen, C$_1$-C$_{12}$alkyl, C$_1$-C$_{12}$hydroxyalkyl, C$_1$-C$_{12}$cyanoalkyl, C$_5$-C$_{30}$aryl or C$_6$-C$_{36}$aralkyl,
Z$_1$ and Z$_2$ are each independently of the other bromine, chlorine, cyano, nitro or trifluoromethyl, but radicals of formula (1a) wherein Z$_1$ and Z$_2$ are chlorine are excluded,
Z$_3$ is bromine, chlorine, cyano, nitro, trifluoromethyl or C$_1$-C$_{12}$alkyl,
Z$_4$ is chlorine or —CONH$_2$,
Z$_5$ is chlorine, bromine, C$_1$-C$_{12}$alkyl or C$_1$-C$_{12}$alkoxy,
Z$_6$ and Z$_7$ are each independently of the other hydrogen, bromine, chlorine, cyano, nitro or trifluoromethyl,
Z$_8$ is cyano, nitro or C$_1$-C$_{12}$alkoxycarbonyl,
Z$_9$ is hydrogen, bromine, chlorine, C$_1$-C$_{12}$alkyl, C$_5$-C$_{30}$aryl or C$_6$-C$_{36}$aralkyl, and
Z$_{10}$ is hydrogen, cyano, nitro or —COR$_4$, wherein R$_4$ is as defined above.
When any of the radicals R$_1$-R$_9$ or Z$_1$-Z$_{10}$ is alkyl, that radical or those radicals may be straight-chain or branched.

Examples of alkyl groups are methyl, ethyl, n-propyl, isopropyl, n-butyl, isobutyl, sec-butyl, tert-butyl, n-pentyl, neopentyl, n-hexyl, n-heptyl, n-octyl, isooctyl, n-decyl and n-dodecyl.

Substituted alkyl groups are, for example, 2-hydroxyethyl, 2-hydroxypropyl, 4-hydroxybutyl, 2-aminoethyl, 2-aminopropyl, 4-aminobutyl, cyanomethyl, 2-cyanoethyl, 2-chloroethyl, 2-bromoethyl and 4-chlorobutyl.

Examples of alkoxy groups are methoxy, ethoxy, n-propoxy, isopropoxy, n-butoxy, isobutoxy, sec-butoxy, tert-butoxy, n-pentyloxy, neopentyloxy, n-hexyloxy, n-heptyloxy, n-octyloxy, isooctyloxy, n-decyloxy and n-dodecyloxy.

Suitable halogen substituents are fluorine and especially chlorine and bromine.

The aryl radicals designated R$_8$, R$_9$, R$_{10}$ or Z$_9$ have preferably from 5 to 24 carbon atoms, especially from 6 to 14 carbon atoms.

Examples of suitable aryl groups are phenyl, tolyl, mesityl, isityl, 2-hydroxyphenyl, 4-hydroxyphenyl, 2-chlorophenyl, 4-chlorophenyl, 2,6-dichlorophenyl, 2-aminophenyl, 3-aminophenyl, 4-aminophenyl, 4-methoxyphenyl, 4-ethoxyphenyl, naphthyl and phenanthryl.

Aralkyl groups as R$_3$, R$_{10}$ or Z$_9$ have preferably from 6 to 30 carbon atoms, especially from 7 to 12 carbon atoms.

Examples of suitable aralkyl groups are benzyl, 2-phenylethyl, tolylmethyl, mesitylmethyl and 4-chlorophenylmethyl.

Heteroaryl as R$_5$, R$_6$, R$_7$ or R$_8$ contains preferably 4 or 5 carbon atoms and one or two hetero atoms from the group O, S and N. It may be, for example, pyrrolyl, furyl, thiophenyl, oxazolyl, thiazolyl, pyridyl, pyrazinyl, pyrimidinyl, pyridazinyl, indolyl, purinyl or quinolyl.

In formula (1), R$_1$ is preferably hydrogen, methyl or methoxy, especially hydrogen.

Also preferred are dyes of formula (1) wherein R$_2$ is hydrogen, methyl, chlorine, acetylamino, propionylamino or methoxyacetylamino.

Dyes of formula (1) wherein R$_2$ is methyl or acetylamino are especially preferred.

In formula (1), R$_3$ is preferably hydrogen, methyl, ethyl, n-propyl, allyl, 1-methoxycarbonylethyl, 2-methoxyethyl, 2-ethoxyethyl, 2-acetoxyethyl, 2-cyanoethyl, 2-methoxycarbonylethyl or 2-ethoxycarbonylethyl.

Special preference is given to dyes of formula (1) wherein R$_3$ is ethyl or 2-methoxyethyl.

R$_4$ in formula (1) is preferably hydrogen or methyl, especially hydrogen.

Y in formula (1) is preferably —CO—.

Preference is given to dyes of formula (1) wherein R$_4$ is hydrogen, n is 0 and m is 2 or 3.

Also preferred are dyes of formula (1) wherein R$_5$, R$_6$ and R$_7$ are each hydrogen.

The radical Ar in formula (1) is derived from the amines Ar—NH$_2$ suitable for diazotisation. Diazo components Ar—NH$_2$ suitable for the preparation of azo dyes are well known to the person skilled in the art.

Examples of suitable radicals Ar are

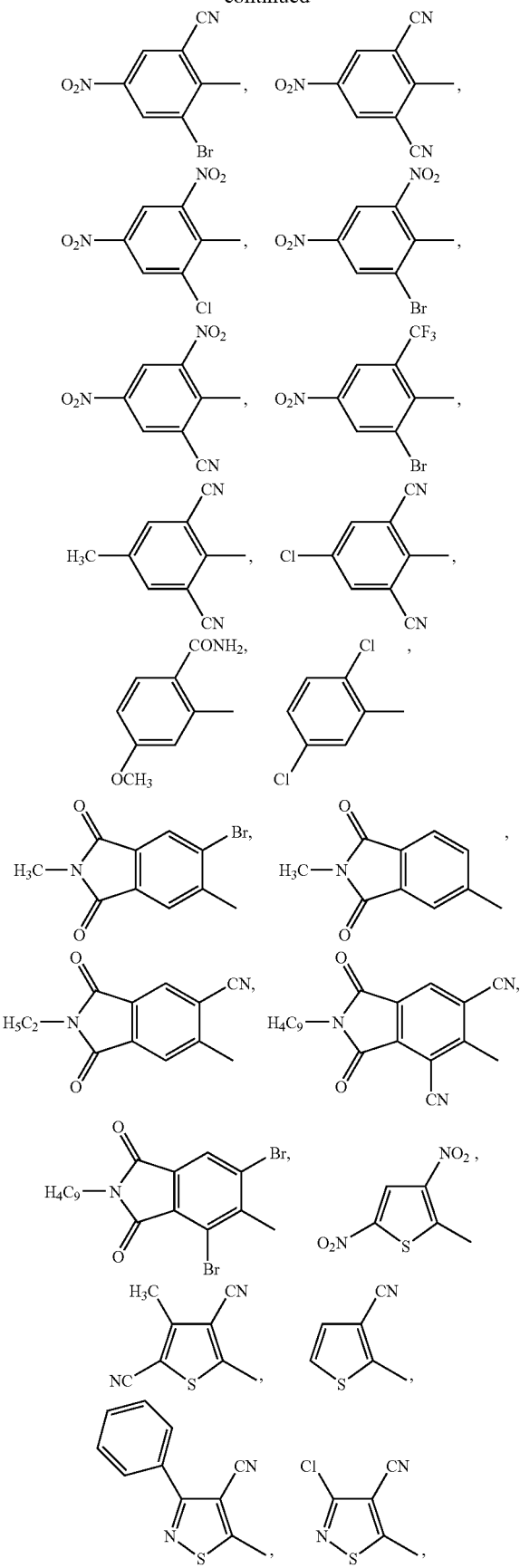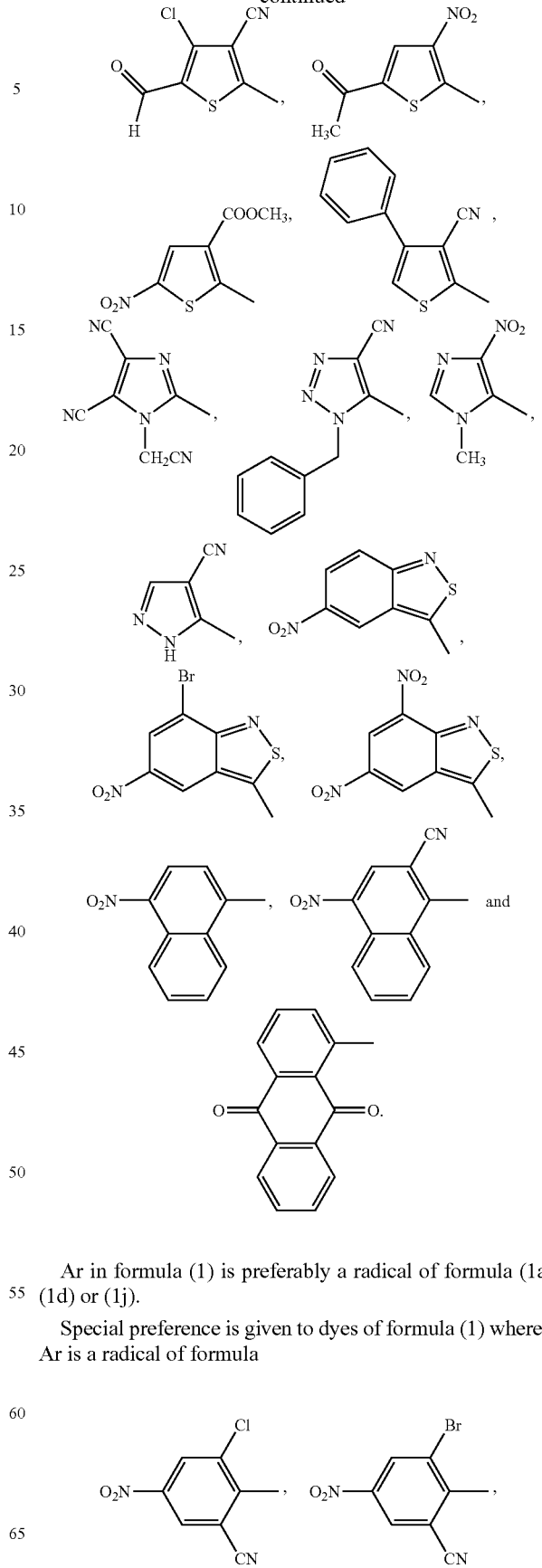
Ar in formula (1) is preferably a radical of formula (1a), (1d) or (1j).
Special preference is given to dyes of formula (1) wherein Ar is a radical of formula

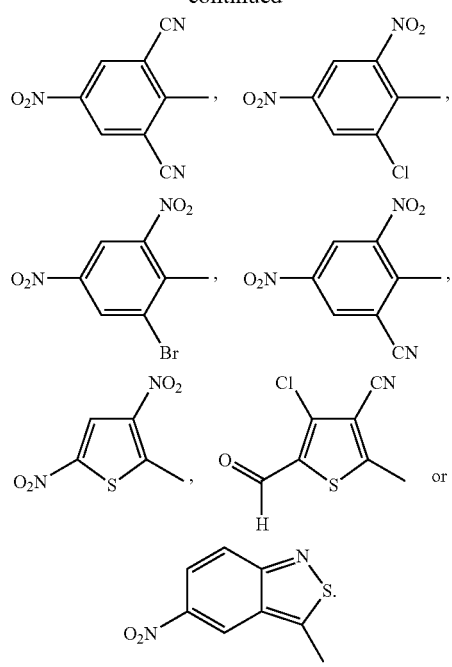
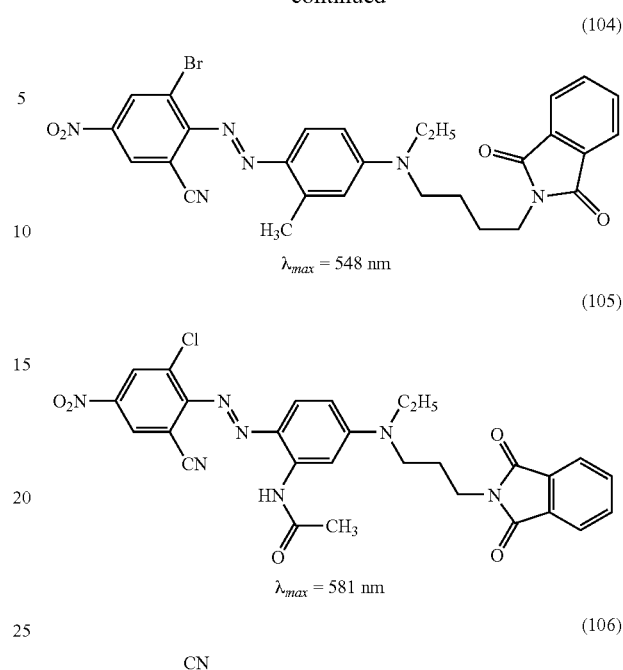
Examples of suitable dyes of formula (1) are the compounds of formulae (101)-(200) ($\lambda_{max}$=wavelength of the absorption maximum):
(101)
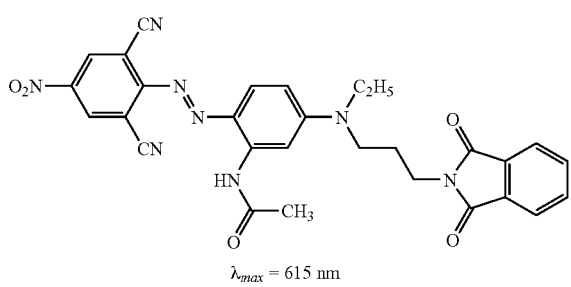
$\lambda_{max}$ = 615 nm
(102)
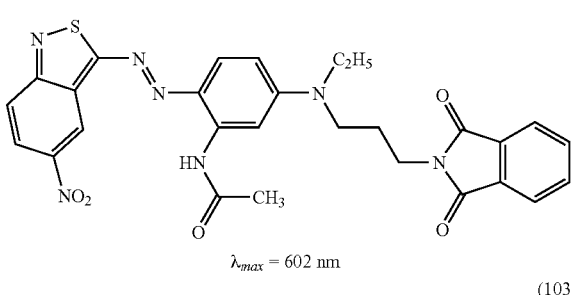
$\lambda_{max}$ = 602 nm
(103)
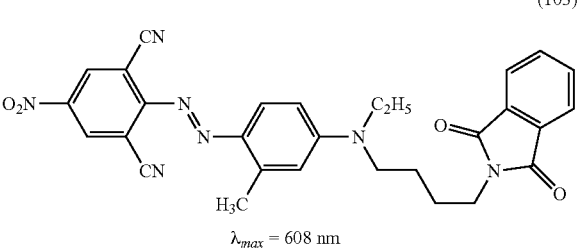
$\lambda_{max}$ = 608 nm
(104)
$\lambda_{max}$ = 548 nm
(105)
$\lambda_{max}$ = 581 nm
(106)
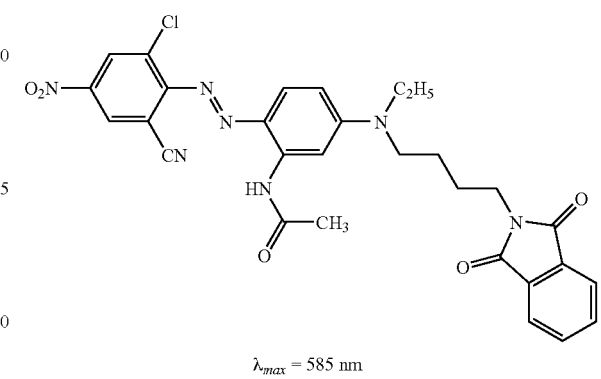
$\lambda_{max}$ = 605 nm
(107)
$\lambda_{max}$ = 585 nm
(108)
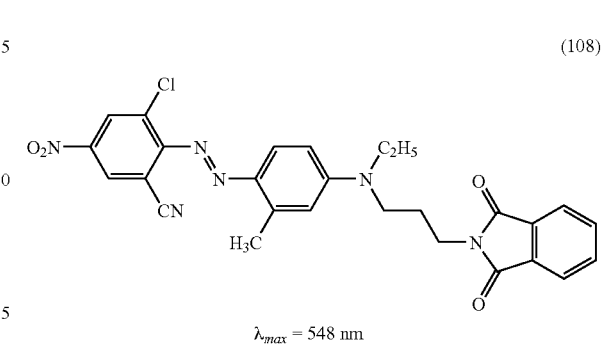
$\lambda_{max}$ = 548 nm

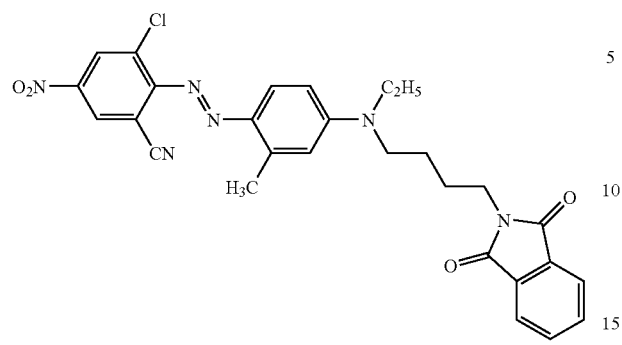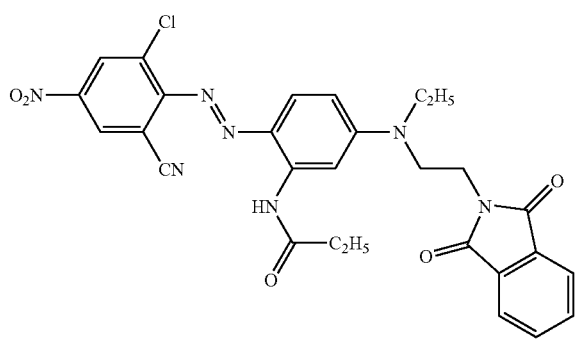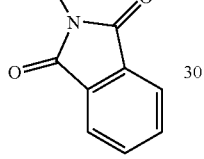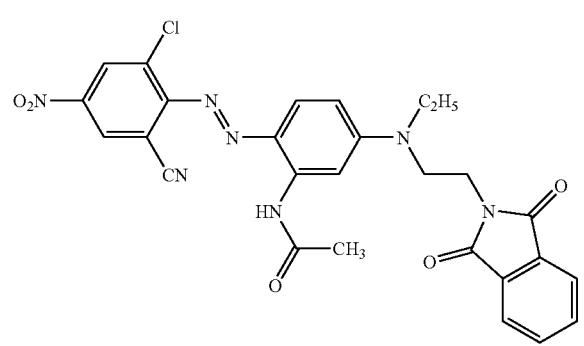

-continued
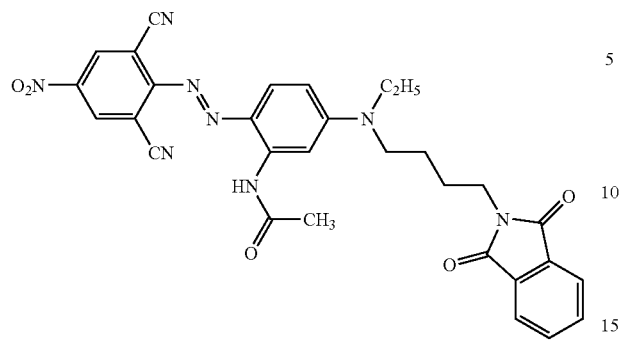
(117)
λ$_{max}$ = 619 nm
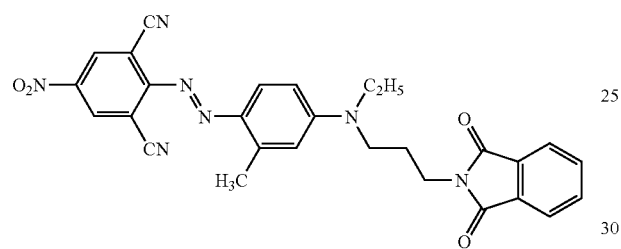
(118)
λ$_{max}$ = 583 nm
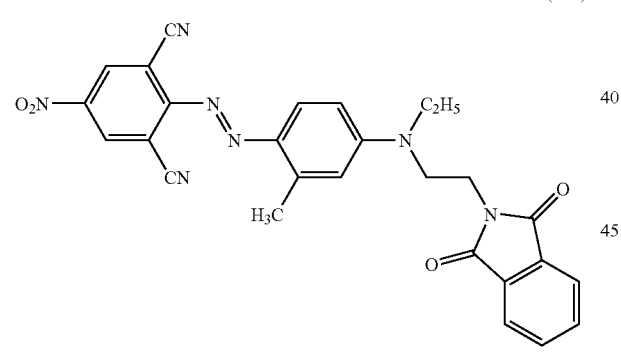
(119)
λ$_{max}$ = 582 nm
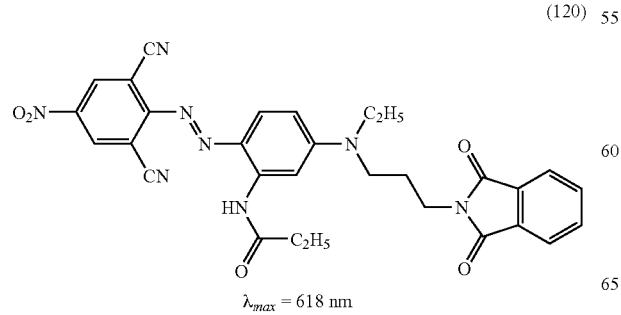
(120)
λ$_{max}$ = 618 nm
-continued
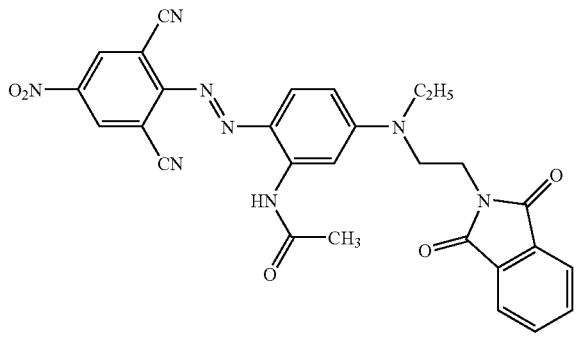
(121)
λ$_{max}$ = 613 nm
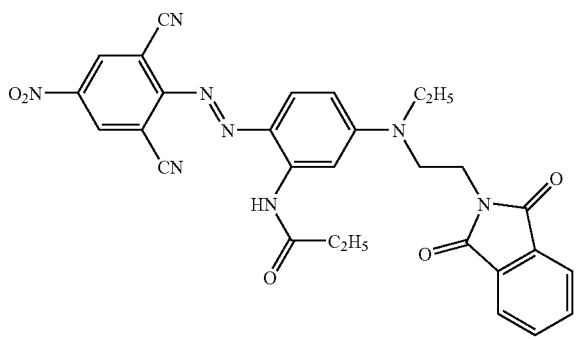
(122)
λ$_{max}$ = 615 nm
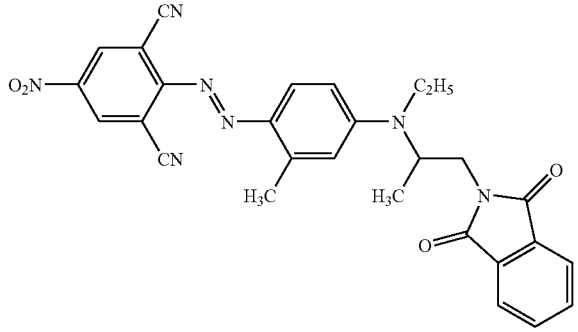
(123)
λ$_{max}$ = 586 nm
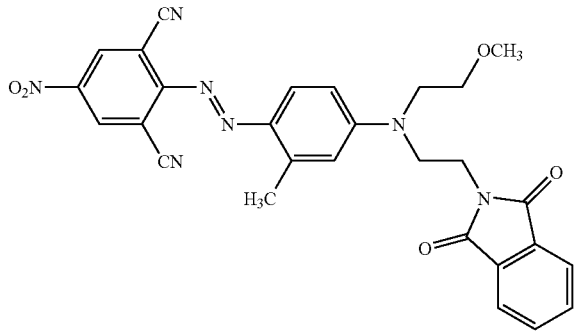
(124)
λ$_{max}$ = 584 nm (125)
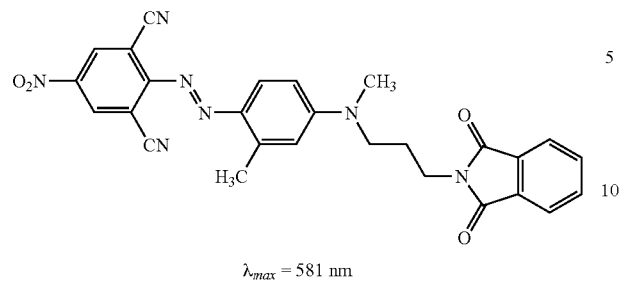
λ_max = 581 nm
(126)
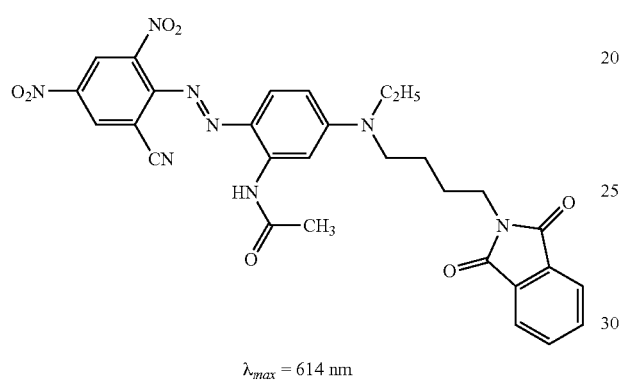
λ_max = 614 nm
(127)
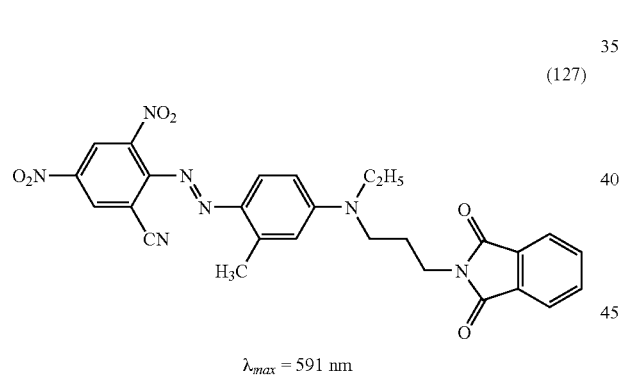
λ_max = 591 nm
(128)
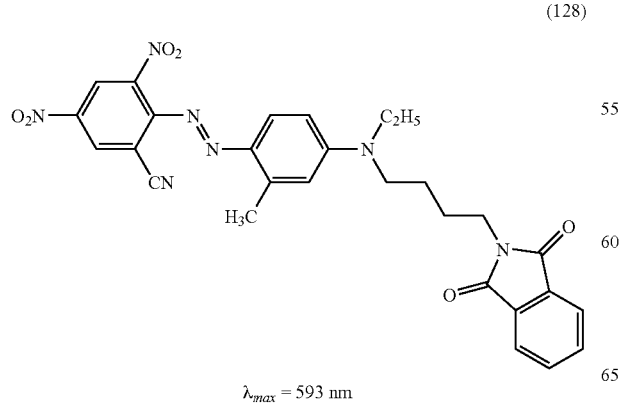
λ_max = 593 nm
(129)
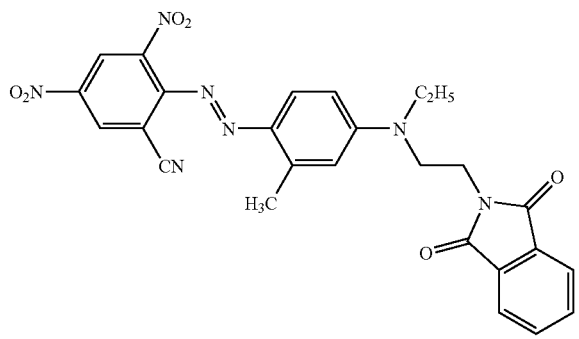
λ_max = 589 nm
(130)
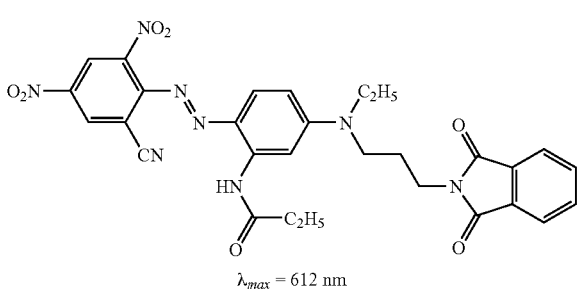
λ_max = 612 nm
(131)
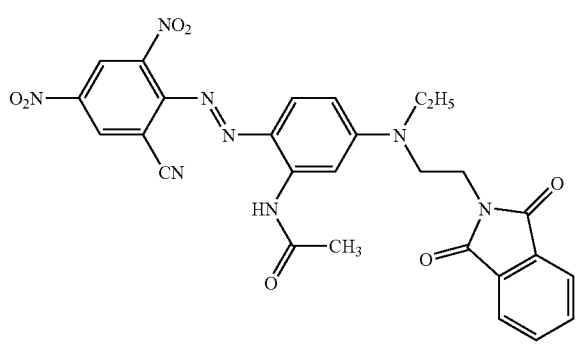
λ_max = 610 nm
(132)
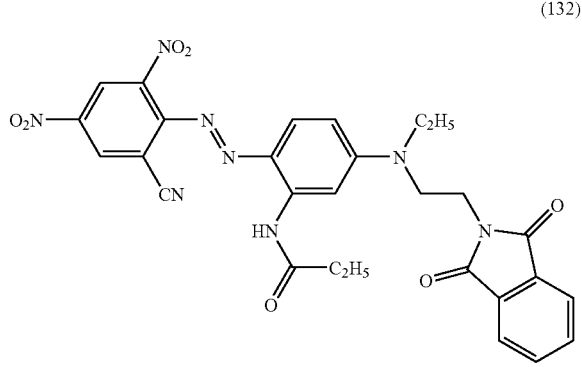
λ_max = 611 nm

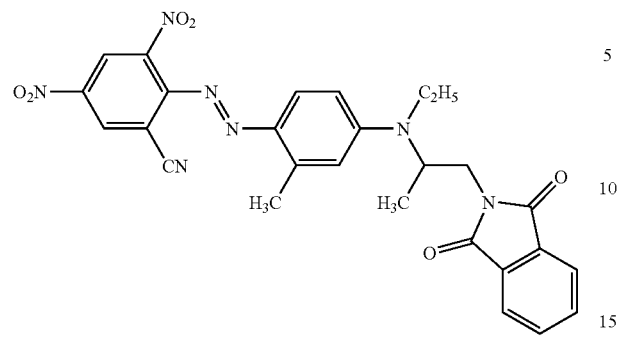
(133) λ$_{max}$ = 592 nm
(134) λ$_{max}$ = 587 nm
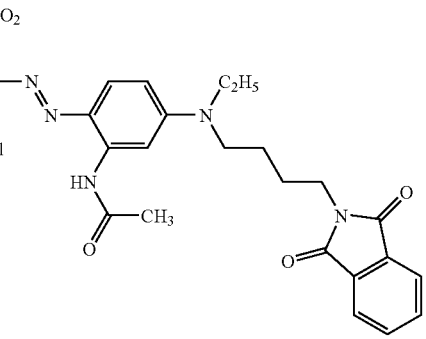
(137) λ$_{max}$ = 559 nm
(138) λ$_{max}$ = 544 nm
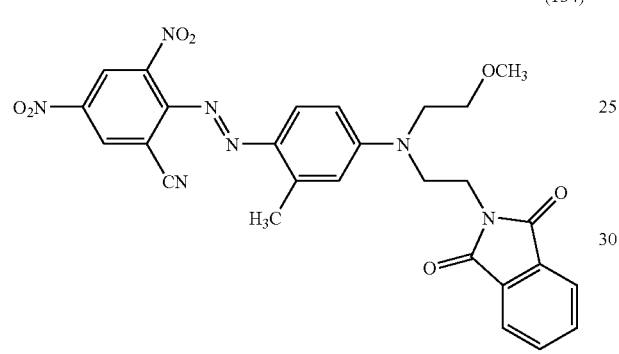
(135) λ$_{max}$ = 587 nm
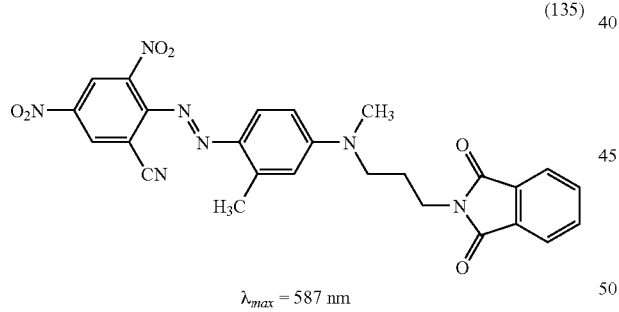
(139) λ$_{max}$ = 546 nm
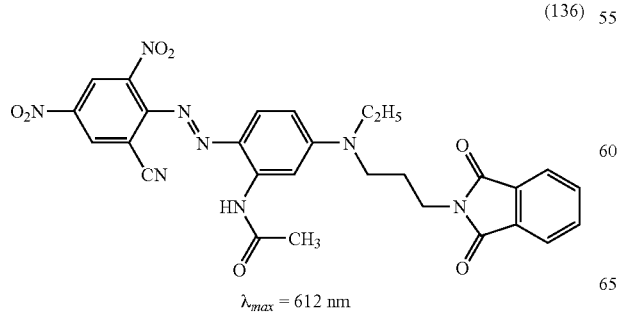
(136) λ$_{max}$ = 612 nm
(140) λ$_{max}$ = 542 nm -continued
(141)
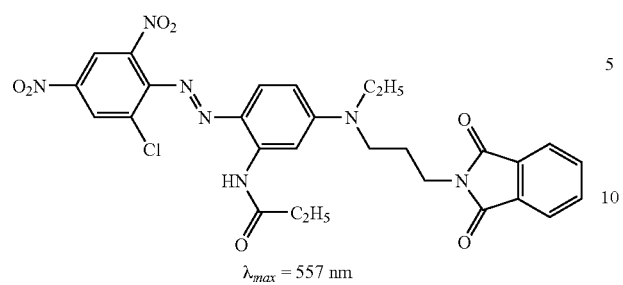
λ_max = 557 nm
(142)
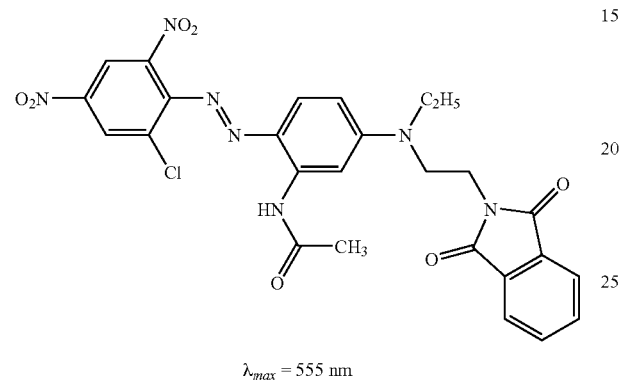
λ_max = 555 nm
(143)
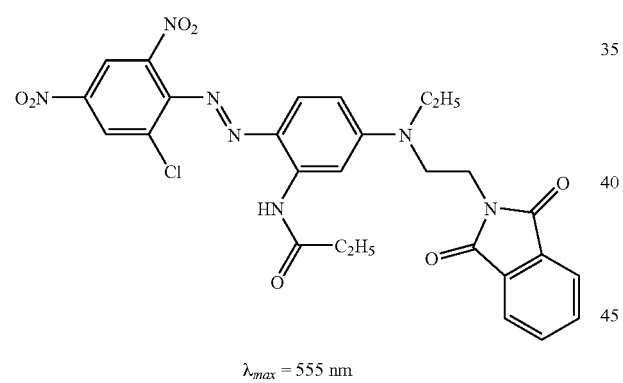
λ_max = 555 nm
(144)
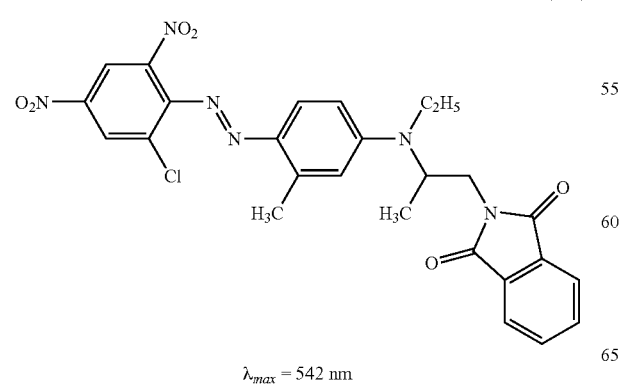
λ_max = 542 nm
-continued
(145)
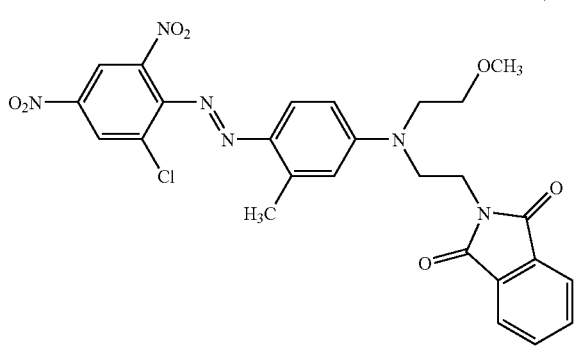
λ_max = 539 nm
(146)
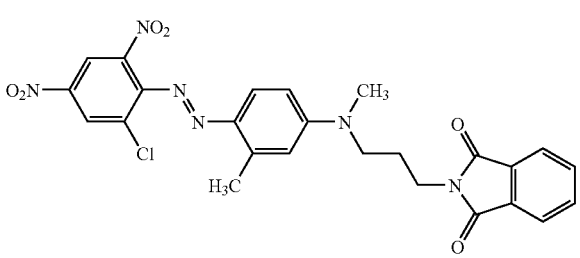
λ_max = 543 nm
(147)
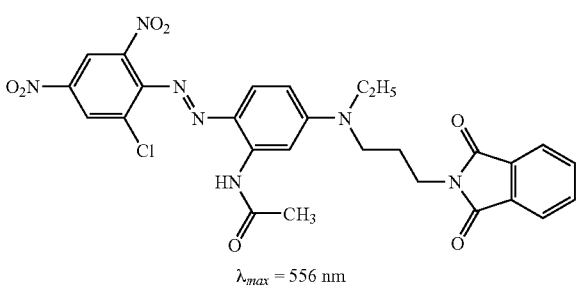
λ_max = 556 nm
(148)
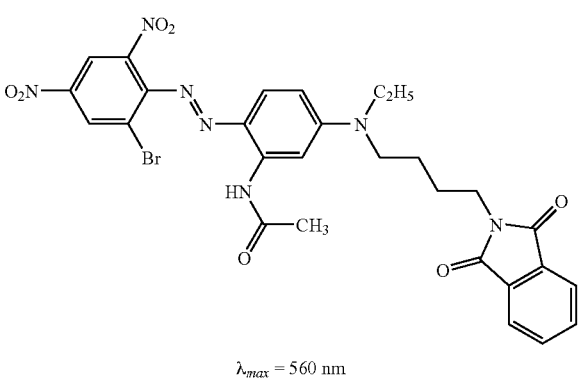
λ_max = 560 nm -continued
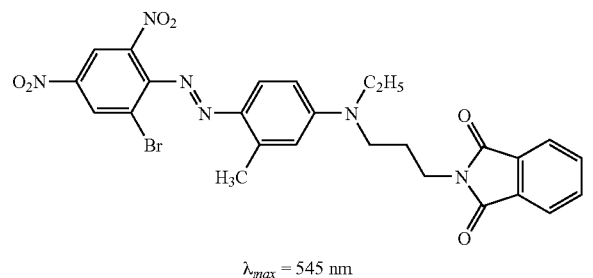
(149)
λ$_{max}$ = 545 nm
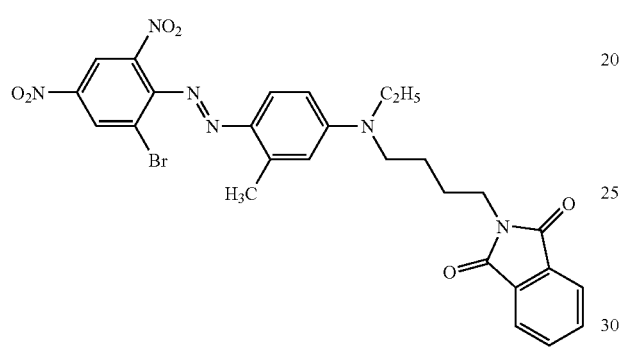
(150)
λ$_{max}$ = 547 nm
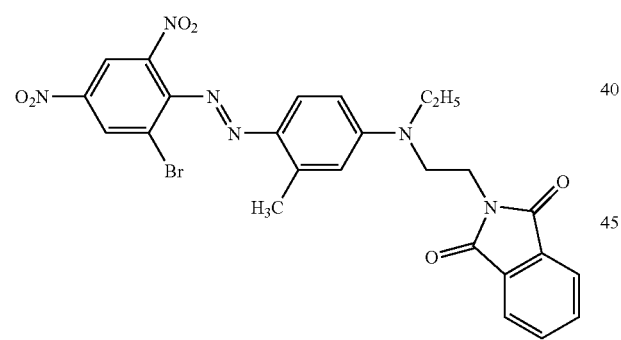
(151)
λ$_{max}$ = 543 nm
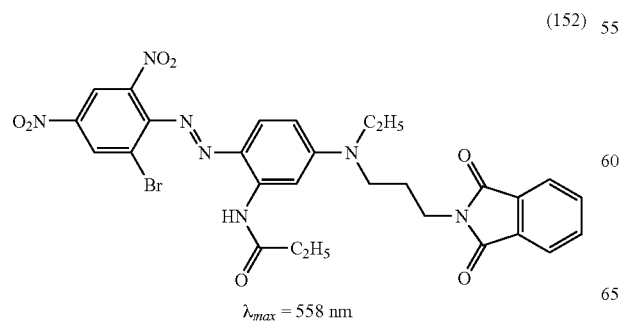
(152)
λ$_{max}$ = 558 nm
-continued
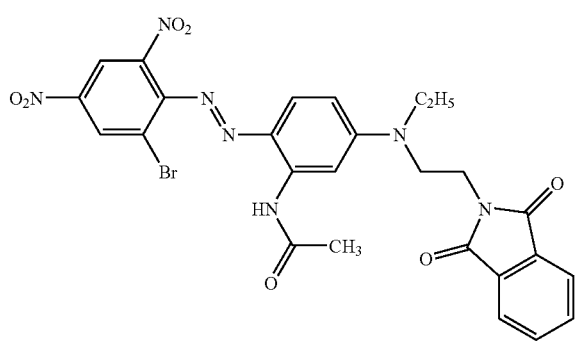
(153)
λ$_{max}$ = 556 nm
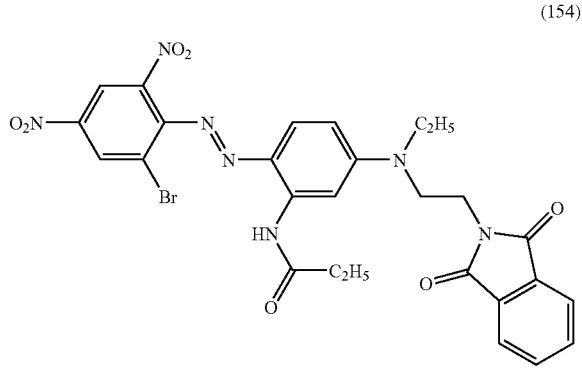
(154)
λ$_{max}$ = 556 nm
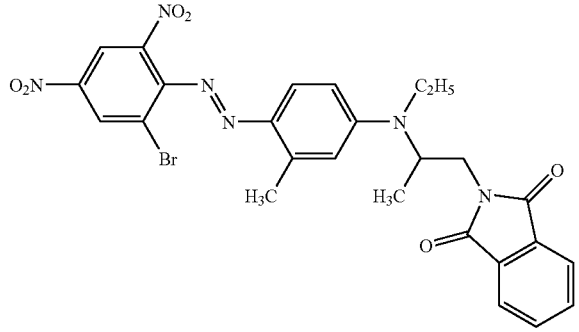
(155)
λ$_{max}$ = 545 nm
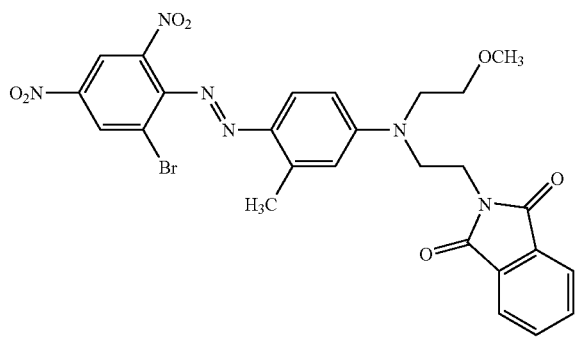
(156)
λ$_{max}$ = 541 nm -continued
(157)
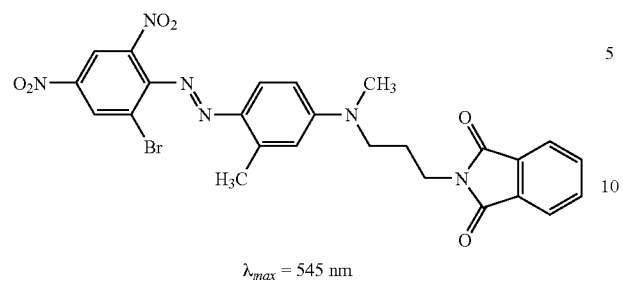
λ<sub>max</sub> = 545 nm
(158)
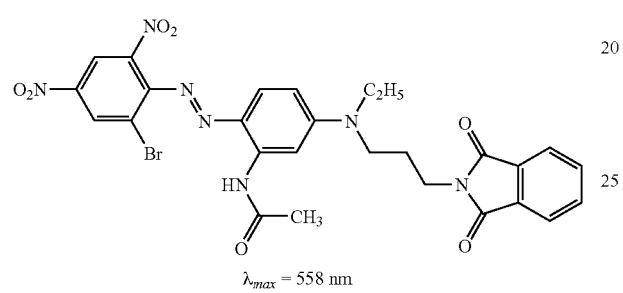
λ<sub>max</sub> = 558 nm
(159)
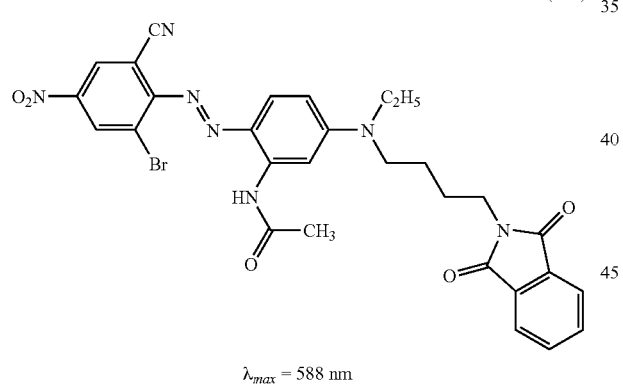
λ<sub>max</sub> = 588 nm
(160)
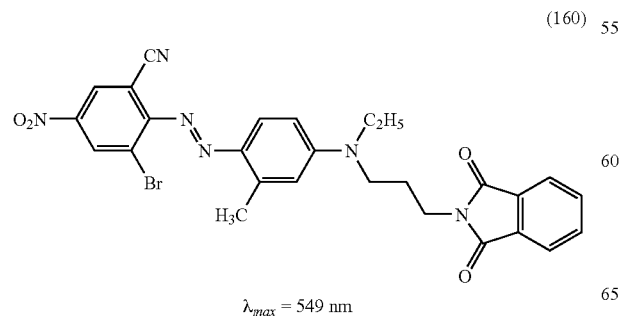
λ<sub>max</sub> = 549 nm
-continued
(161)
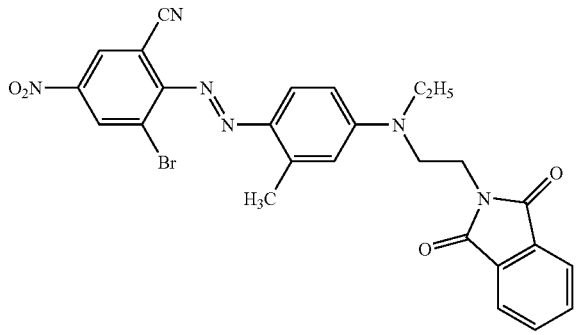
λ<sub>max</sub> = 547 nm
(162)
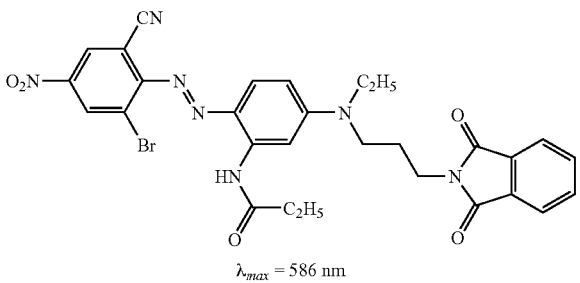
λ<sub>max</sub> = 586 nm
(163)
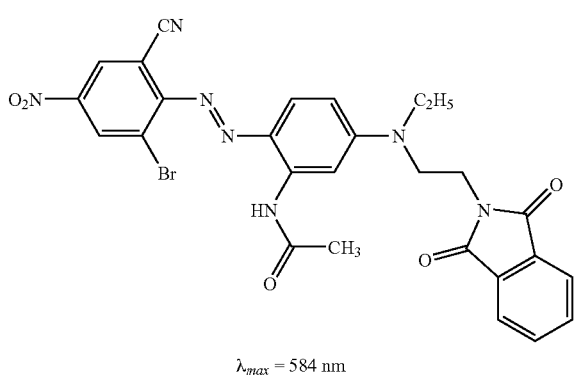
λ<sub>max</sub> = 584 nm
(164)
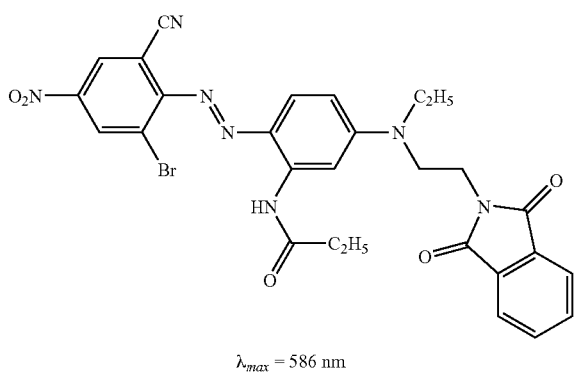
λ<sub>max</sub> = 586 nm -continued
(165)
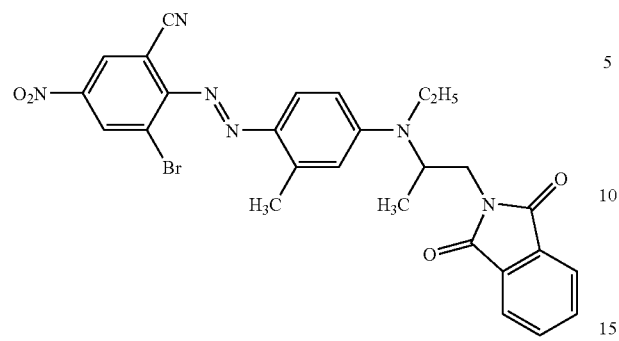
λ_max = 549 nm
(166)
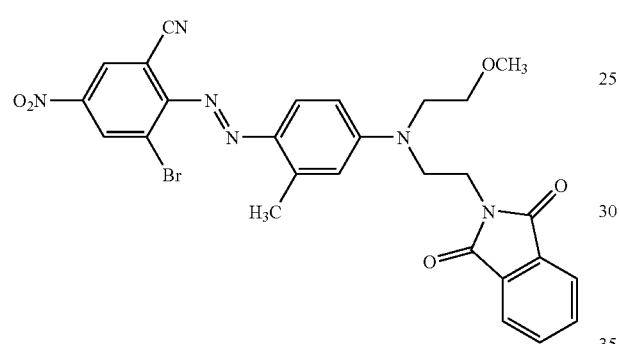
λ_max = 544 nm
(167)
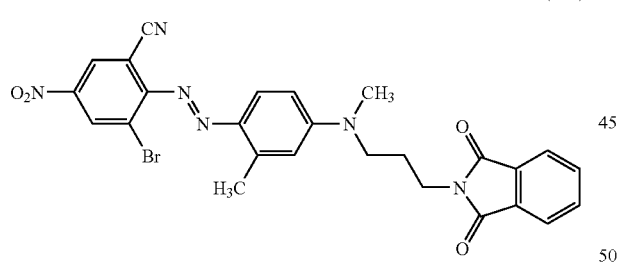
λ_max = 546 nm
(168)
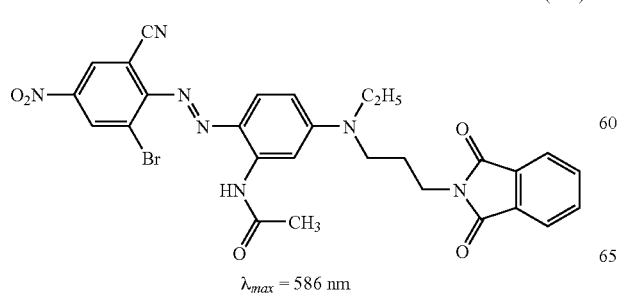
λ_max = 586 nm
-continued
(169)
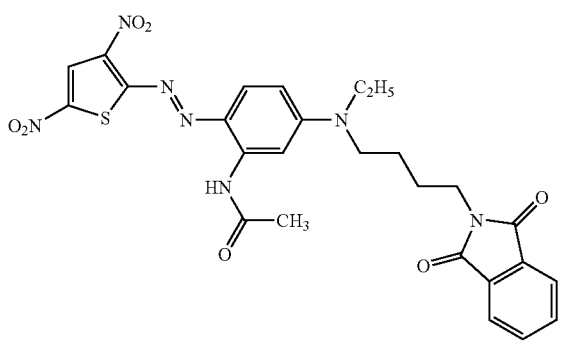
λ_max = 640 nm
(170)
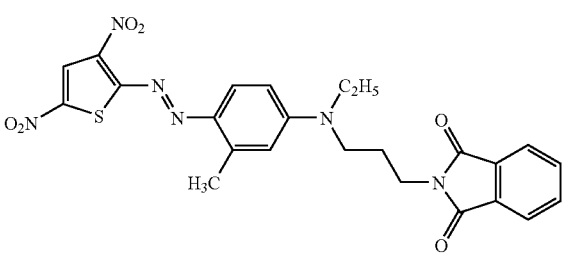
λ_max = 638 nm
(171)
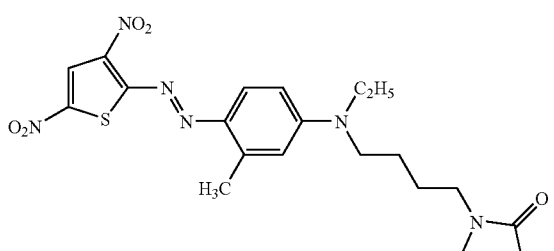
λ_max = 640 nm
(172)
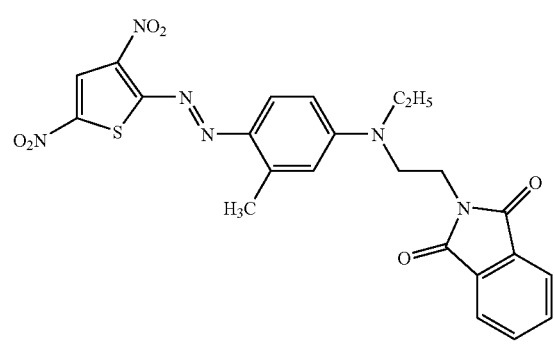
λ_max = 637 nm (173)
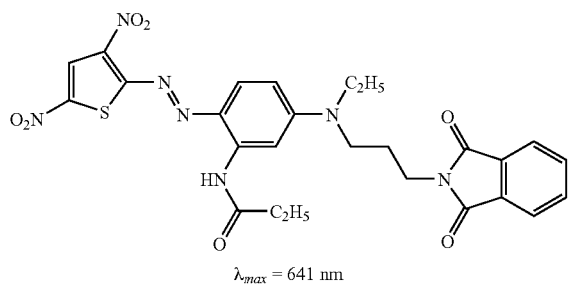
λ_max = 641 nm
(174)
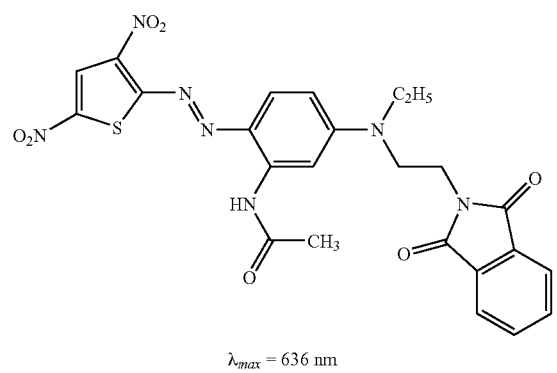
λ_max = 636 nm
(175)
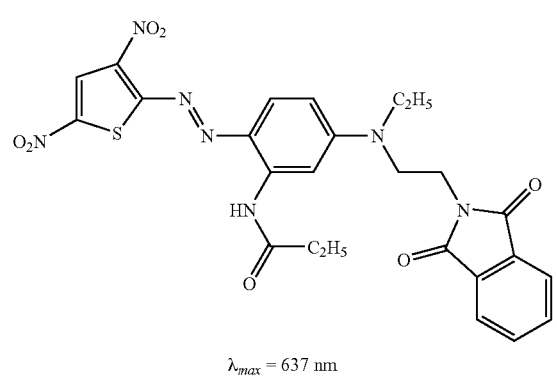
λ_max = 637 nm
(176)
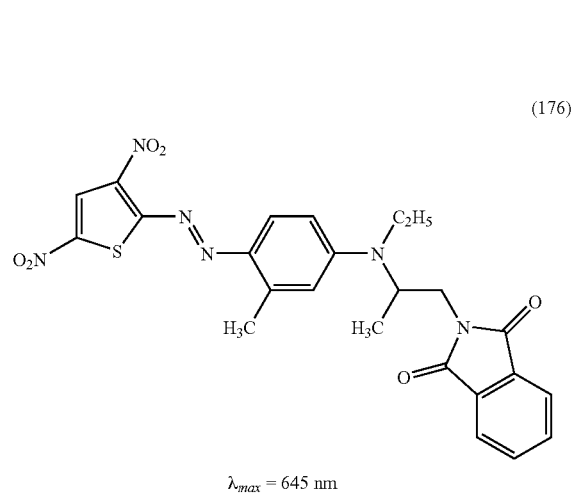
λ_max = 645 nm
(177)
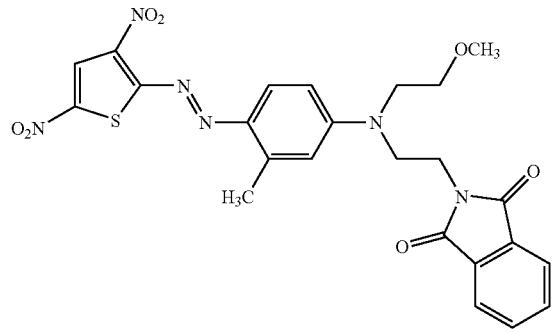
λ_max = 635 nm
(178)
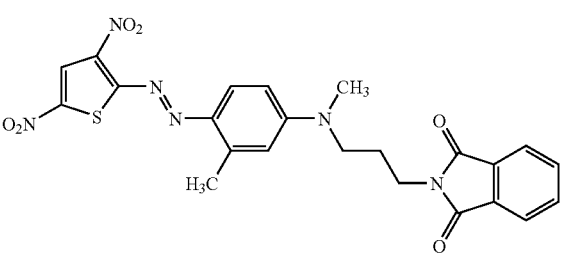
λ_max = 640 nm
(179)
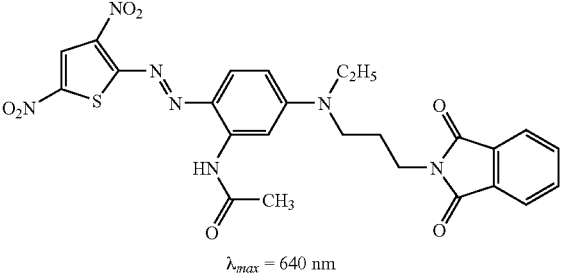
λ_max = 640 nm
(180)
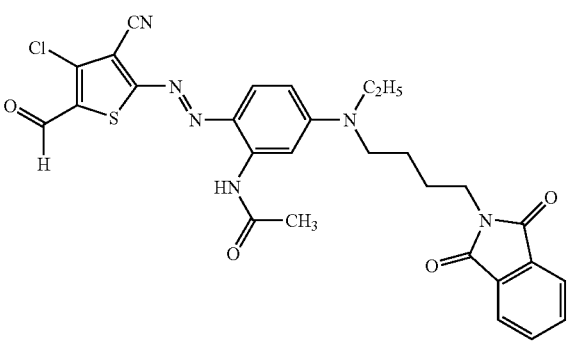
λ_max = 610 nm -continued (181) λ_max = 610 nm (182) λ_max = 613 nm (183) λ_max = 607 nm (184) λ_max = 609 nm (185) λ_max = 607 nm (186) λ_max = 608 nm (187) λ_max = 609 nm (188) λ_max = 604 nm (189)
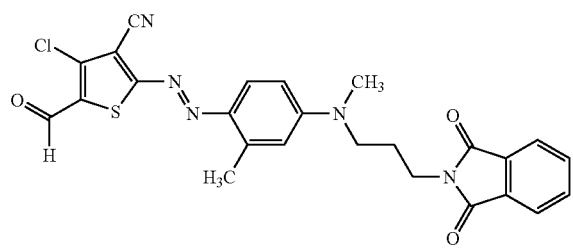
λ<sub>max</sub> = 606 nm
(190)
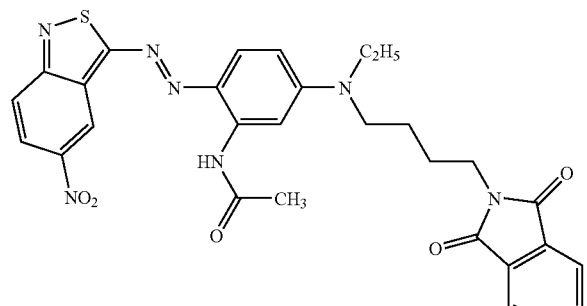
λ<sub>max</sub> = 608 nm
(191)
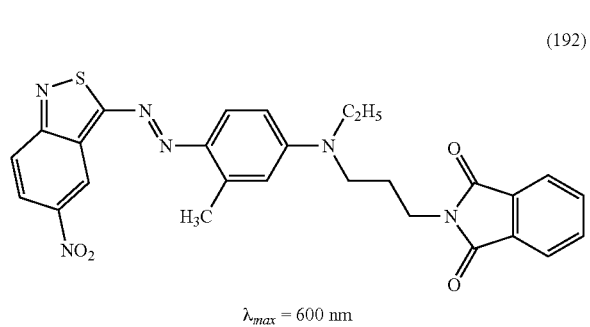
λ<sub>max</sub> = 605 nm
(192)
λ<sub>max</sub> = 600 nm
(193)
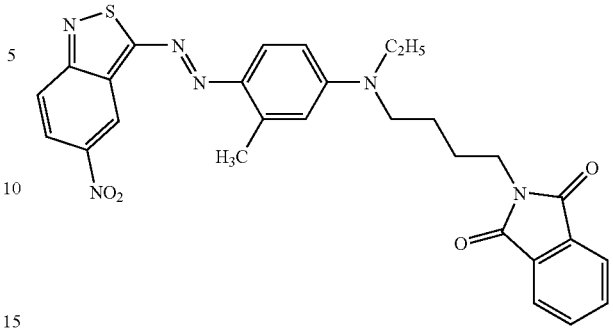
λ<sub>max</sub> = 601 nm
(194)
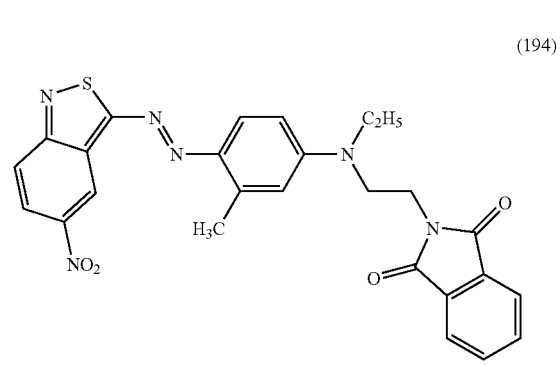
λ<sub>max</sub> = 597 nm
(195)
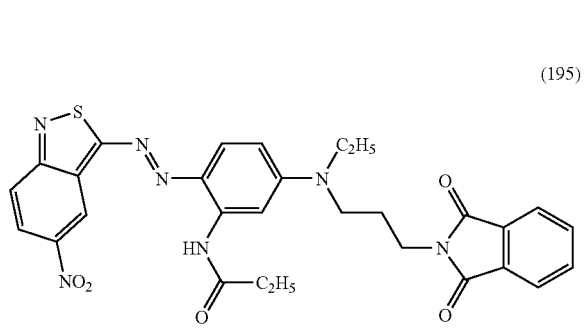
λ<sub>max</sub> = 603 nm
(196)
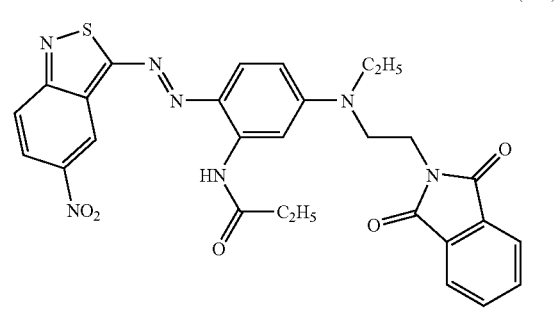
λ<sub>max</sub> = 600 nm -continued
(197)
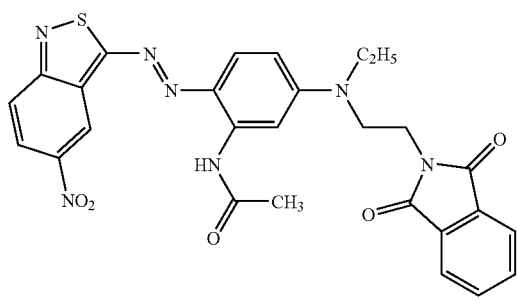
λ_max = 600 nm
(198)
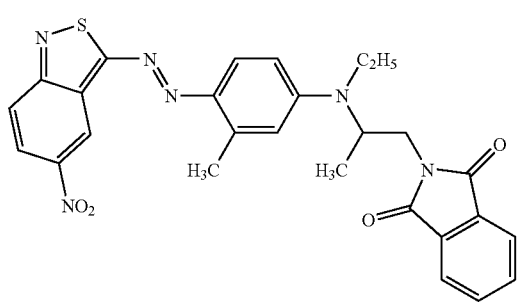
λ_max = 601 nm
(199)
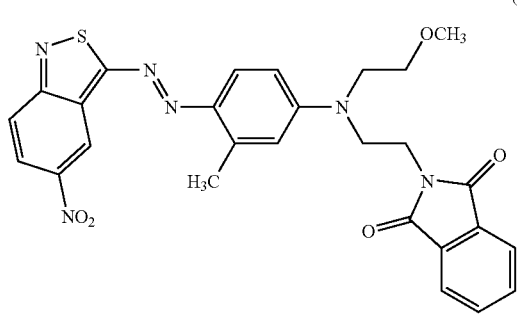
λ_max = 597 nm
(200)
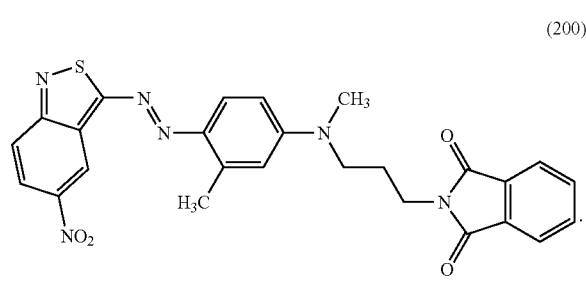
λ_max = 599 nm
Special preference is given to the dyes of formulae (101)-(106)
(101)
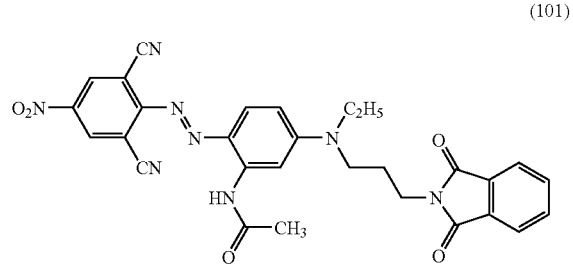
(102)
(103)
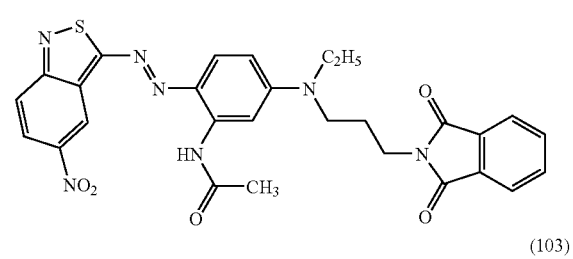
(104)
(105)
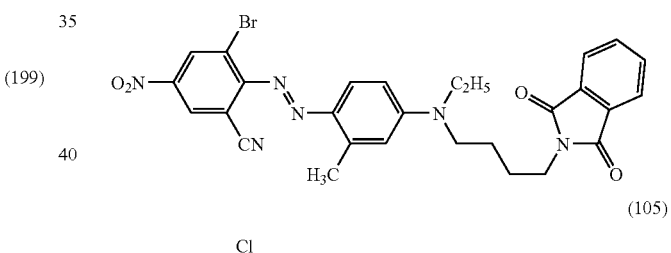
(106)
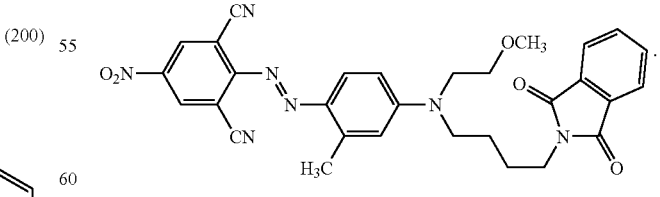
The invention relates also to the process for the preparation of a dye of formula (1) wherein a dam component of formula Ar—NH$_2$, wherein Ar is as defined above, is diazotised and coupled to a coupling component of formula (2)

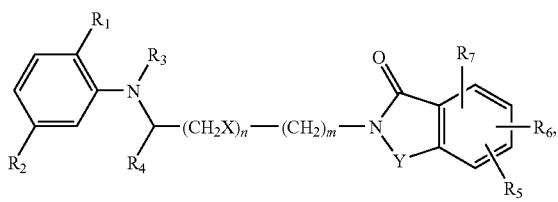

(2)

wherein $R_1$ to $R_7$, X, n, m and Y are as defined above.

The coupling component of formula (2) is novel and the invention relates also thereto.

The coupling component of formula (2) can be synthesised in accordance with processes known per se, for example by condensing a compound of formula (3) with a compound of formula (4),

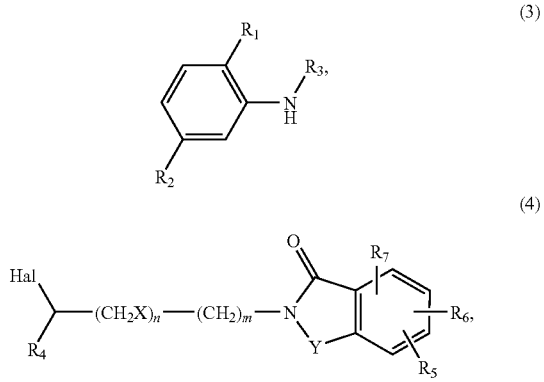

wherein in formulae (3) and (4) $R_1$ to $R_7$, X, n, m and Y are as defined above and Hal is halogen.

The anilines of formula (3) are known and some are commercially available.

The halogen compounds of formula (4) are likewise known or are obtainable by known methods, for example by the process described in WO 2003/027070.

The invention relates also to the process for the preparation of the coupling component of formula (2).

The diazotisation is carried out in a manner known per se, for example with sodium nitrite in an acidic, e.g. hydrochloric-acid-containing or sulfuric-acid-containing, aqueous medium. The diazotisation may, however, also be carried out using other diazotisation agents, for example using nitrosylsulfuric acid. In the diazotisation, an additional acid may be present in the reaction medium, for example phosphoric acid, sulfuric acid, acetic acid, propionic acid or hydrochloric acid or a mixture of such acids, for example a mixture of propionic acid and acetic acid. The diazotisation is advantageously carried out at temperatures of from −10 to 30° C., for example from −10° C. to room temperature.

The coupling of the diazotised compound to the coupling component of formula (2) is likewise effected in known manner, for example in an acidic, aqueous or aqueous-organic medium, advantageously at temperatures of from −10 to 30° C., especially below 10° C. Examples of acids used are hydrochloric acid, acetic acid, propionic acid, sulfuric acid and phosphoric acid.

The diazo components Ar—$NH_2$ are known or can be prepared in a known manner.

The present invention relates also to dye mixtures comprising at least one dye of formula (1) and at least one dye other than of formula (1).

Suitable dyes other than of formula (1) that can be used in the dye mixtures according to the invention are, for example, the azo dyes of formulae (I), (II), (III), (IV) and (V) described in WO 2006/131530, the dyes described in Examples 1-5 of WO 2005/056690 and the azo dyes of formula (I) disclosed in WO 2005/040283.

Further suitable dyes which can advantageously be mixed with the dyes of formula (1) according to the invention are, for example, C.I. Disperse Violet 107, C.I. Disperse Blue 60, C.I. Disperse Blue 284, C.I. Disperse Blue 295, C.I. Disperse Blue 337, C.I. Disperse Blue 354, C.I. Disperse Blue 365, C.I. Disperse Blue 368, C.I. Disperse Blue 378, C.I. Disperse Blue 380.

The dye mixtures according to the invention can be prepared, for example, by simply mixing the individual dyes.

The amount of the individual dyes in the dye mixtures according to the invention can vary within a wide range.

The dye mixtures according to the invention advantageously contain at least 20% by weight, preferably at least 30% by weight and especially at least 40% by weight, of one or more dyes of formula (1).

The dyes and dye mixtures according to the invention can be used in the dyeing or printing of semi-synthetic and, especially, synthetic hydrophobic fibre materials, more especially textile materials. Textile materials composed of blends that contain such semi-synthetic and/or synthetic hydrophobic fibre materials can likewise be dyed or printed using the dyes or dye mixtures according to the invention.

Semi-synthetic fibre materials that come into consideration are especially cellulose 2½ acetate and cellulose triacetate.

Synthetic hydrophobic fibre materials consist especially of linear, aromatic polyesters, for example those of terephthalic acid and glycols, especially ethylene glycol, or condensation products of terephthalic acid and 1,4-bis(hydroxymethyl)cyclohexane; of polycarbonates, for example those of α,α-dimethyl-4,4-dihydroxy-diphenylmethane and phosgene, and of fibres based on polyvinyl chloride and on polyamide.

The application of the dyes and dye mixtures according to the invention to the fibre materials is effected in accordance with known dyeing procedures. For example, polyester fibre materials are dyed in the exhaust process from an aqueous dispersion in the presence of customary anionic or non-ionic dispersants and optionally customary swelling agents (carriers) at temperatures of from 80 to 140° C. Cellulose 2½ acetate is dyed preferably at from 65 to 85° C. and cellulose triacetate at temperatures of from 65 to 115° C.

The dyes and dye mixtures according to the invention will not colour wool and cotton present at the same time in the dyebath or will colour such materials only slightly (very good reservation), so that they can also be used satisfactorily in the dyeing of polyester/wool and polyester/cellulosic fibre blend fabrics.

The dyes and dye mixtures according to the invention are suitable for dyeing in accordance with the thermosol process, in the exhaust process and for printing processes.

The said fibre materials can be in a variety of processing forms, e.g. in the form of fibres, yarns or non-wovens, in the form of woven fabrics or knitted fabrics.

It is advantageous to convert the dyes and dye mixtures according to the invention into a dye preparation prior to use. For that purpose, the dye is ground so that its particle size is on average from 0.1 to 10 microns. The grinding can be carried out in the presence of dispersants. For example, the dried dye is ground with a dispersant or is kneaded in paste form with a dispersant and then dried in vacuo or by atomisation. The preparations so obtained can be used, after the addition of water, to prepare print pastes and dyebaths.

For printing, the customary thickeners will be used, e.g. modified or unmodified natural products, for example alginates, British gum, gum arabic, crystal gum, locust bean flour, tragacanth, carboxymethylcellulose, hydroxyethylcellulose, starch or synthetic products, for example polyacrylamides, polyacrylic acid or copolymers thereof, or polyvinyl alcohols.

The dyes and dye mixtures according to the invention impart to the mentioned materials, especially to polyester materials, level colour shades having very good in-use fastness properties, such as, especially, good fastness to light, to thermofixing, to pleating, to chlorine and to wetting, such as fastness to water, to perspiration and to washing; the finished dyeings are also distinguished by very good fastness to rubbing. Special mention should be made of the good fastness properties of the resulting dyeings in respect of light, perspiration and, especially, washing.

The dyes and dye mixtures according to the invention can also be used satisfactorily in the preparation of mixed shades together with other dyes.

The dyes and dye mixtures according to the invention are also very suitable for dyeing hydrophobic fibre materials from supercritical $CO_2$.

The present invention relates also to the above-mentioned use of the dyes and dye mixtures according to the invention as well as to a process for the dyeing or printing of semi-synthetic or synthetic hydrophobic fibre materials, especially textile materials, wherein a dye according to the invention is applied to the said materials or is incorporated into those materials. The said hydrophobic fibre materials are preferably textile polyester materials. Further substrates that can be treated by the process according to the invention as well as preferred process conditions can be found above in the detailed description of the use of the dyes according to the invention.

The invention relates also to hydrophobic fibre materials, especially polyester textile materials, dyed or printed by the said process.

The dyes according to the invention are also suitable for modern reproduction processes, for example thermotransfer printing.

The following Examples serve to illustrate the invention. In the Examples, unless otherwise indicated, parts are parts by weight and percentages are percent by weight. The temperatures are given in degrees Celsius. The relationship between parts by weight and parts by volume is the same as that between grams and cubic centimeters.

PREPARATION EXAMPLES

Example I.1

A. Preparation of the Coupling Component 9.3 g (0.05 mol) of dry 3-acetamido-N-ethylaniline are heated to 110° C., and 2 ml of toluene and 6.2 g of sodium acetate are added thereto. With vigorous stirring, a solution of 21.63 g (0.07 mol) of N-(4-bromobutyl) phthalimide in 25 ml of toluene is slowly added dropwise at 130° C. and the acetic acid formed in the mixture is continuously distilled off. The mixture is then allowed to cool to 100° C. and the volatile constituents that still remain are separated off by distillation under reduced pressure. The viscous oil that remains behind is stirred with a small amount of methanol/water (1:1) and the aqueous phase is separated off. The pure product crystallised from ethanol/water (1:1) has a melting point of 80° C.; the yield is 14.0 g (75%).

B. Diazotisation 21 g of 40% nitrosylsulfuric acid are placed in a laboratory reaction apparatus. At 15-20° C., 6.1 g of 2,6-dibromo-4-nitroaniline are introduced. After being stirred for 2 hours at 15-20° C., the mixture is poured into 60 g of ice-water and stirred for a further 15 min. The excess nitrite is destroyed by addition of sulfamic acid.

C. Coupling 7.4 g of 4-acetylamino-N-(3-phthalimidopropyl)-N-ethylaniline in 50 ml of 80% acetic acid are placed in a laboratory reaction apparatus and 3 drops of Surfynol 104 E (2,4,7,9-tetra-methyl-5-decyne-4,7-diol) are added thereto. After addition of 40 g of ice, the solution of the diazonium salt prepared under B is slowly added dropwise so that the internal temperature is 0-5° C. The mixture is stirred for 1 hour at 0-5° C. and overnight at RT. After addition of 100 ml of water, the solid is filtered off with suction, washed with deionised water and dried. 13.1 g of the compound of formula (101a) are obtained.

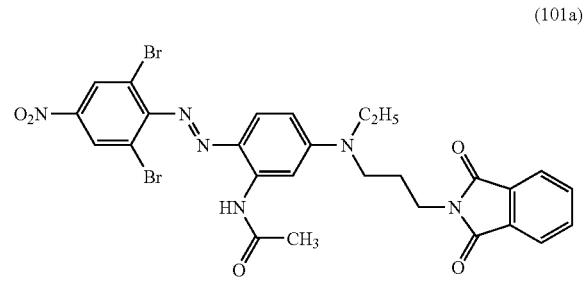

(101a)

D. Cyanation

A solution of 4.15 g of the dye (101a) in 80 ml of DMF is added dropwise in the course of 30 min at 105° C. to a solution of 1.37 g of CuCN and 0.15 g of NaCN in 100 ml of DMF. The mixture is stirred for 2 hours at 105° C. After cooling to RT, 15 ml of water are added dropwise and stirring is then carried out overnight at RT. The solid is then filtered off with suction, washed with 15% $NH_3$ solution and with water and dried.

Yield: 3.0 g of the dye of formula (101).

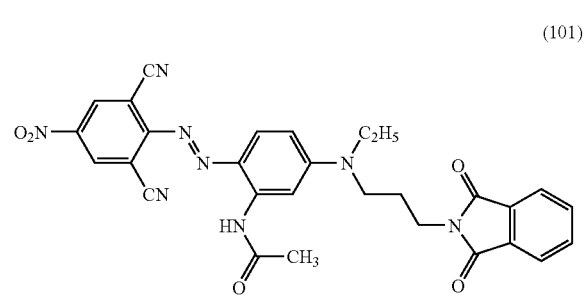

(101)

Examples I.2-I.6

The dyes (102)-(106) are prepared analogously to the process described in Example I.1.

(102)
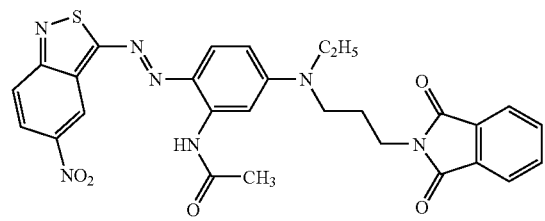

(103)
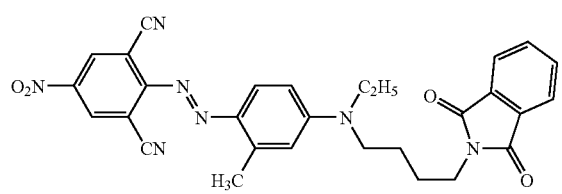

(104)
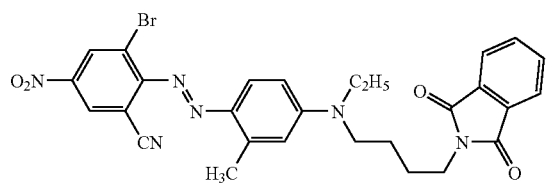

(105)
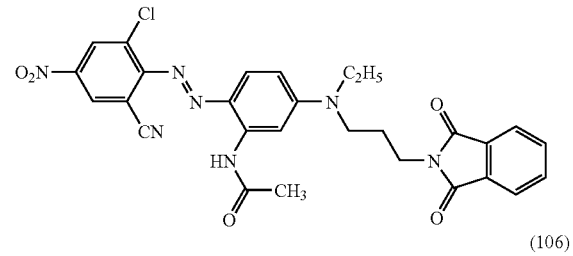

(106)
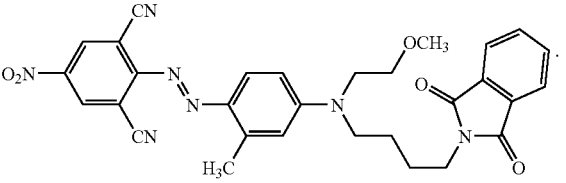

II. APPLICATION EXAMPLES

Example II.1

Samples of a polyester fabric (Tersuisse 5-4204) are dyed in a high-temperature exhaust process at 135° C. in a dyebath containing 1% of one of the dyes (101)-(105). The resulting dyeings exhibit fastness values in respect of sublimation, washing and perspiration of $\geq 4$.

Example II.2

As described in Example II.1, samples of a polyester fabric are dyed, but instead of the dyes (101)-(105) the dye mixtures 1-48 given in Table 1 are used. The numerical data given in Table 1 denote % by weight in each case.

The dyeings so obtained exhibit high fastness values in respect of sublimation, washing and perspiration.

TABLE 1

| Dye | 1 | 2 | 3 | 4 | 5 | 6 | 7 | 8 | 9 | 10 | 11 | 12 |
|---|---|---|---|---|---|---|---|---|---|---|---|---|
| Compound (101) | | | | | 20 | | | | | | | |
| Compound (102) | 15 | 20 | 40 | 35 | | 30 | | | | | | |
| Compound (103) | 50 | 40 | | | 60 | 40 | 40 | 60 | 50 | 55 | 45 | 45 |
| Compound (104) | | 40 | | | | | | | | | | |
| Compound (105) | 35 | | | | | 30 | | | | | | |
| Compound (106) | | | | | | | | | | | | |
| Disperse Blue 60 | | | | | 20 | | | | | | | |
| Disperse Blue 284 | | | | | | | | | | | | |
| Disperse Blue 354 | | | | | | | 50 | | | 25 | 30 | |
| Disperse Blue 368 | | | | | | | | 40 | | | | |
| Disperse Blue 378 | | | | 65 | | | | | | | | |
| Disperse Blue 380 | | | 60 | | | | | | 30 | 15 | 15 | |
| Disperse Blue 365 | | | | | | | | | | | | |
| Disperse Blue 337 | | | | | | | | | | | | 55 |
| DS Violet 107 | | | | | | | 10 | | 20 | 5 | 10 | |
| Disperse Blue 295 | | | | | | | | | | | | |

| Dye | 13 | 14 | 15 | 16 | 17 | 18 | 19 | 20 | 21 | 22 | 23 | 24 |
|---|---|---|---|---|---|---|---|---|---|---|---|---|
| Compound (101) | | | | | 50 | 40 | 40 | | 35 | 35 | | 20 |
| Compound (102) | | | | | | | | | | | | |
| Compound (103) | | | | | | | 30 | 40 | | 35 | | |
| Compound (104) | | 50 | | | | 10 | | 25 | 35 | 30 | | |
| Compound (105) | 50 | | | | | | 30 | | | | | |
| Compound (106) | | | 60 | 55 | | | | | 30 | | 65 | |
| Disperse Blue 60 | | | | | 30 | | | | | | | |
| Disperse Blue 284 | | | | | | | | 35 | | | 35 | |
| Disperse Blue 354 | | | | 30 | | | | | | | | |
| Disperse Blue 368 | | 40 | | | | | | | | | | |
| Disperse Blue 378 | | | | | | | 40 | | | | | 50 |

TABLE 1-continued

| | 25 | 26 | 27 | 28 | 29 | 30 | 31 | 32 | 33 | 34 | 35 | 36 |
|---|---|---|---|---|---|---|---|---|---|---|---|---|
| Disperse Blue 380 | | | | | | | | | | | | |
| Disperse Blue 365 | | | | | | | | | | | | |
| Disperse Blue 337 | 50 | 50 | | | 20 | | | | | | | 30 |
| DS Violet 107 | | | | 15 | | 10 | | | | | | |
| Disperse Blue 295 | | | | | | | | | | | | |

| Dye | 25 | 26 | 27 | 28 | 29 | 30 | 31 | 32 | 33 | 34 | 35 | 36 |
|---|---|---|---|---|---|---|---|---|---|---|---|---|
| Compound (101) | 40 | | | | | 25 | | | | 30 | 45 | 35 |
| Compound (102) | | | | | | 25 | | 60 | 50 | 20 | | |
| Compound (103) | | 25 | 30 | | 50 | | 45 | | | | | 65 |
| Compound (104) | | | | | | | | | | | | |
| Compound (105) | | | | 50 | | | | | | | | |
| Compound (106) | | 25 | 15 | | | | | | | | | |
| Disperse Blue 60 | | | | | | 50 | | 40 | | 15 | | |
| Disperse Blue 284 | | | | 50 | | | | | | | | |
| Disperse Blue 354 | | 50 | 45 | | 30 | | 40 | | | | | |
| Disperse Blue 368 | | | | | | | | | | | | |
| Disperse Blue 378 | 35 | | | | | | | | | | | |
| Disperse Blue 380 | | | | | | | | | | | | |
| Disperse Blue 365 | | | | | | | | | | | | |
| Disperse Blue 337 | 25 | | | | | | | | | | | |
| DS Violet 107 | | | 10 | | 20 | | 15 | | | | | |
| Disperse Blue 295 | | | | | | | | | 50 | 35 | 55 | |

| Dye | 37 | 38 | 39 | 40 | 41 | 42 | 43 | 44 | 45 | 46 | 47 | 48 |
|---|---|---|---|---|---|---|---|---|---|---|---|---|
| Compound (101) | | | | | | 50 | 50 | | | | 20 | |
| Compound (102) | | 30 | | | | | | | | | 20 | 30 |
| Compound (103) | 50 | | | | | | | | 60 | 35 | 20 | |
| Compound (104) | | | | | | | | 35 | | | | |
| Compound (105) | 50 | | 30 | 30 | 50 | | 25 | 35 | | | 20 | |
| Compound (106) | | | | | | | | | | 35 | 20 | |
| Disperse Blue 60 | | 40 | | | | | | | | | | |
| Disperse Blue 284 | | | | | | | | | | | | |
| Disperse Blue 354 | | | | | | | | | | | | 30 |
| Disperse Blue 368 | | | 70 | | | | | | | | | |
| Disperse Blue 378 | | | | | | | | | | | | |
| Disperse Blue 380 | | | | 70 | | | | 30 | | | | |
| Disperse Blue 365 | | | | | | | | | | | | 40 |
| Disperse Blue 337 | | | | | 50 | 50 | 25 | | | | | |
| DS Violet 107 | | | | | | | | | 40 | 30 | | |
| Disperse Blue 295 | | 30 | | | | | | | | | | |

What is claimed is:

1. A dye of formula

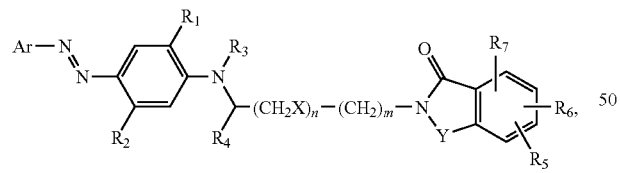
(1)

wherein Ar is a radical of formula (1a)-(1g), 1(i)-(1l)

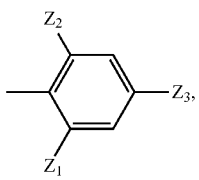
(1a)

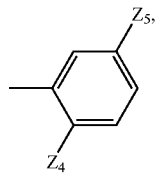
(1b)

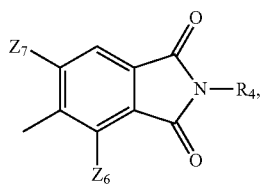
(1c)

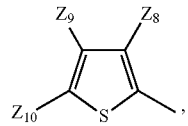
(1d)

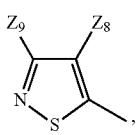
(1e)

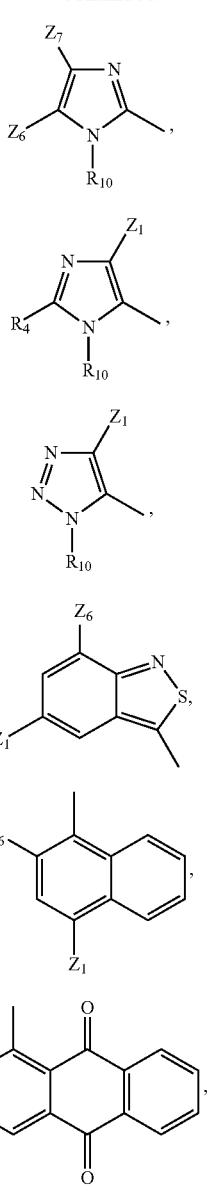

wherein
- R₁ is hydrogen, $C_1$-$C_{12}$ alkyl, $C_1$-$C_{12}$ alkoxy or halogen,
- R₂ is hydrogen, $C_1$-$C_{12}$ alkyl, halogen or —NHCOR₈, wherein R₈ is $C_1$-$C_{12}$ alkyl unsubstituted or substituted by one or more $C_1$-$C_{12}$ alkoxy groups, hydroxyl groups, amino groups or halogen atoms; $C_5$-$C_{30}$ aryl unsubstituted or substituted by one or more $C_1$-$C_{12}$ alkyl groups, $C_1$-$C_{12}$ alkoxy groups, hydroxyl groups, amino groups or halogen atoms; or $C_5$-$C_{30}$ heteroaryl unsubstituted or substituted by one or more $C_1$-$C_{12}$ alkyl groups, $C_1$-$C_{12}$ alkoxy groups, hydroxyl groups, amino groups or halogen atoms,
- R₃ is $C_1$-$C_{12}$ alkyl unsubstituted or substituted by one or more $C_1$-$C_{12}$ alkoxy groups, hydroxyl groups, amino groups, —COOR₈ groups, —OCOR₈ groups, wherein R₈ is as defined above, or halogen atoms; $C_2$-$C_{12}$ alkenyl unsubstituted or substituted by one or more $C_1$-$C_{12}$ alkoxy groups, hydroxyl groups, amino groups or halogen atoms; or $C_6$-$C_{36}$ aralkyl unsubstituted or substituted by one or more $C_1$-$C_{12}$ alkoxy groups, hydroxyl groups, amino groups or halogen atoms,
- R₄ is hydrogen or $C_1$-$C_{12}$ alkyl,
- X is oxygen or sulfur,
- n is 0,
- m is 2 or 3,
- Y is —CO—,
- R₅, R₆ and R₇ are each independently of the others hydrogen, $C_1$-$C_{12}$ alkyl, $C_1$-$C_{12}$ alkoxy, halogen, —CN, —NO₂, —CF₃, —COOR₉ or —CONHR₉, wherein R₉ is $C_1$-$C_{12}$ alkyl, $C_5$-$C_{30}$ aryl or $C_5$-$C_{30}$ heteroaryl,
- R₁₀ is hydrogen, $C_1$-$C_{12}$ alkyl, $C_1$-$C_{12}$ hydroxyalkyl, $C_1$-$C_{12}$ cyanoalkyl, $C_5$-$C_{30}$ aryl or $C_6$-$C_{36}$ aralkyl,
- Z₁ and Z₂ are each independently of the other bromine, chlorine, cyano, nitro or trifluoro-methyl, but radicals of formula (1a) wherein Z₁ and Z₂ are chlorine are excluded,
- Z₃ is bromine, chlorine, cyano, nitro, trifluoromethyl or $C_1$-$C_{12}$ alkyl,
- Z₄ is chlorine or —CONH₂,
- Z₅ is chlorine, bromine, $C_1$-$C_{12}$ alkyl or $C_1$-$C_{12}$ alkoxy,
- Z₆ and Z₇ are each independently of the other hydrogen, bromine, chlorine, cyano, nitro or trifluoromethyl,
- Z₈ is cyano, nitro or $C_1$-$C_{12}$ alkoxycarbonyl,
- Z₉ is hydrogen, bromine, chlorine, $C_1$-$C_{12}$ alkyl, $C_5$-$C_{30}$ aryl or $C_6$-$C_{36}$ aralkyl, and
- Z₁₀ is hydrogen, cyano, nitro or —COR₄, wherein R₄ is as defined above.

2. A dye of formula (1) according to claim 1, wherein R₁ is hydrogen, methyl or methoxy.

3. A dye of formula (1) according to claim 1, wherein R₂ is hydrogen, methyl, chlorine, acetylamino, propionylamino or methoxyacetylamino.

4. A dye of formula (1) according to claim 1, wherein R₃ is hydrogen, methyl, ethyl, n-propyl, allyl, 1-methoxycarbonylethyl, 2-methoxyethyl, 2-ethoxyethyl, 2-acetoxyethyl, 2-methoxycarbonylethyl or 2-ethoxycarbonylethyl.

5. A dye of formula (1) according to claim 1, wherein R₄ is hydrogen or methyl.

6. A dye of formula (1) according to claim 1, wherein R₅, R₆ and R₇ are each hydrogen.

7. A dye of formula (1) according to claim 1, wherein Ar is a radical of formula (1a), (1d) or (1j).

8. A dye of formula (1) according to claim 1, wherein Ar is a radical of formula -continued

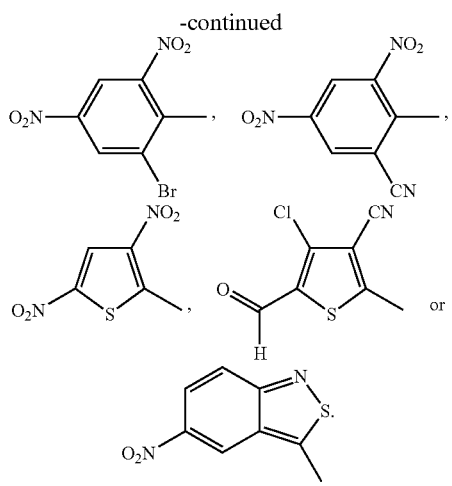

9. A process for the preparation of a dye of formula (1) according to claim 1, wherein a diazo component of formula Ar—NH$_2$, wherein Ar is as defined in claim 1, is diazotised and coupled to a coupling component of formula (2)

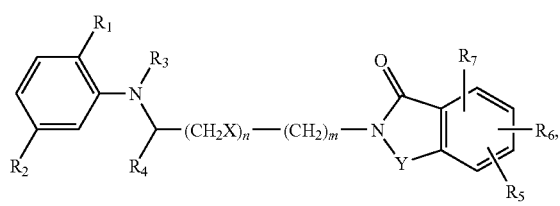
(2)

wherein R$_1$ to R$_7$, X, n, m and Y are as defined in claim 1.

10. A process for the preparation of a compound of formula (2),

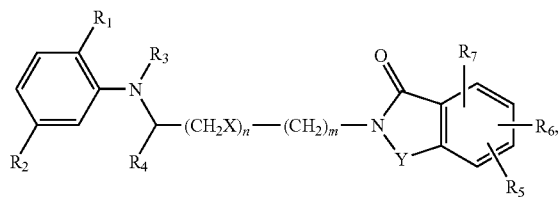
(2)

wherein a compound of formula (3) is condensed with a compound of formula (4),

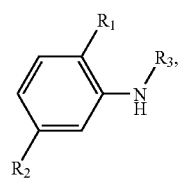
(3)

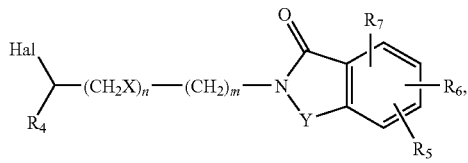
(4)

wherein in formulae (2), (3) and (4)

R$_1$ is hydrogen, C$_1$-C$_{12}$ alkyl, C$_1$-C$_{12}$ alkoxy or halogen,

R$_2$ is hydrogen, C$_1$-C$_{12}$ alkyl, halogen or —NHCOR$_8$, wherein R$_8$ is C$_1$-C$_{12}$ alkyl unsubstituted or substituted by one or more C$_1$-C$_{12}$ alkoxy groups, hydroxyl groups, amino groups or halogen atoms; C$_5$-C$_{30}$ aryl unsubstituted or substituted by one or more C$_1$-C$_{12}$ alkyl groups, C$_1$-C$_{12}$ alkoxy groups, hydroxyl groups, amino groups or halogen atoms; or C$_5$-C$_{30}$ heteroaryl unsubstituted or substituted by one or more C$_1$-C$_{12}$ alkyl groups, C$_1$-C$_{12}$ alkoxy groups, hydroxyl groups, amino groups or halogen atoms, R$_3$ is C$_1$-C$_{12}$ alkyl unsubstituted or substituted by one or more C$_1$-C$_{12}$ alkoxy groups, hydroxyl groups, amino groups, —COOR$_8$ groups, —OCOR$_8$ groups, wherein R$_8$ is as defined above, or halogen atoms; C$_2$-C$_{12}$ alkenyl unsubstituted or substituted by one or more C$_1$-C$_{12}$ alkoxy groups, hydroxyl groups, amino groups or halogen atoms; or C$_6$-C$_{36}$ aralkyl unsubstituted or substituted by one or more C$_1$-C$_{12}$ alkoxy groups, hydroxyl groups, amino groups or halogen atoms, R$_4$ is hydrogen or C$_1$-C$_{12}$ alkyl, X is oxygen or sulfur, n is 0, m is 2 or 3, Y is —CO—, R$_5$, R$_6$ and R$_7$ are each independently of the others hydrogen, C$_1$-C$_{12}$ alkyl, C$_1$-C$_{12}$ alkoxy, halogen, —CN, —NO$_2$, —CF$_3$, —COOR$_9$ or —CONHR$_9$, wherein R$_9$ is C$_1$-C$_{12}$ alkyl, C$_5$-C$_{30}$ aryl or C$_5$-C$_{30}$ heteroaryl, and Hal is halogen.

11. A dye mixture comprising at least one dye of formula (1) according to claim 1 and at least one dye other than of formula (1).

12. A process for the dyeing or printing of a semi-synthetic or synthetic hydrophobic fibre material, wherein a dye of formula (1) according to claim 1 is applied to the said material or is incorporated into that material.

13. A semi-synthetic fibre material dyed or printed by the process according to claim 12.

14. A process for the dyeing or printing of a semi-synthetic or synthetic hydrophobic fibre material, wherein a dye mixture according to claim 11 is applied to the said material or is incorporated into that material.

15. A semi-synthetic fibre material dyed or printed by the process according to claim 14.

* * * * *